United States Patent [19]

Bowler et al.

[11] Patent Number: 4,659,516

[45] Date of Patent: Apr. 21, 1987

[54] STEROID DERIVATIVES

[75] Inventors: Jean Bowler, Sandbach; Brian S. Tait, Macclesfield, both of United Kingdom

[73] Assignee: Imperial Chemical Industries PLC, London, England

[21] Appl. No.: 656,466

[22] Filed: Oct. 1, 1984

[30] Foreign Application Priority Data

Oct. 12, 1983 [GB] United Kingdom ............... 8327256

[51] Int. Cl.⁴ ...................... C07J 00/00; A61K 31/56
[52] U.S. Cl. .................................................. 260/397.5
[58] Field of Search ...................... 260/397.5; 514/182

[56] References Cited

U.S. PATENT DOCUMENTS 3,679,716  7/1972  Anner et al. ................... 260/397.5
4,011,314  3/1977  Petzoldt et al. ................ 260/397.5

Primary Examiner—Leonard Schenkman
Assistant Examiner—Joseph A. Lipovsky
Attorney, Agent, or Firm—Cushman, Darby & Cushman

[57] ABSTRACT

A steroid derivative of the formula:

ST—A—X—R¹ wherein ST is a 7α-linked steroid nucleus of the general formula:

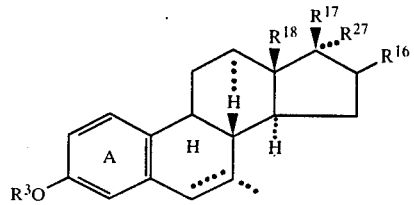

wherein the double bond(s) between carbon atoms 6 and 7 and/or carbon atoms 8 and 9 are optional; wherein the aromatic ring A may optionally bear one or two halogen or alkyl substituents; wherein $R^3$ is hydrogen, alkyl, or acyl; wherein $R^{16}$ is hydrogen, alkyl or hydroxy; wherein either $R^{17}$ is hydroxy or acyloxy and $R^{27}$ is hydrogen, alkyl, alkenyl or alkynyl, or $R^{17}$ and $R^{27}$ together form oxo (=O); wherein $R^{18}$ is alkyl; wherein A is alkylene, alkenylene or alkynylene optionally fluorinated and optionally interrupted by —O—, —S—, —SO—, —SO$_2$—, —CO—, —NR—, —NRCO—, —CONR—, —COO—, —OCO— or phenylene, wherein R is hydrogen or alkyl; wherein $R^1$ is hydrogen, alkyl, alkenyl, cycloalkyl, halogenoalkyl, carboxyalkyl, alkoxycarbonylalkyl, aryl, arylalkyl, or dialkylaminoalkyl, or $R^1$ is joined to $R^2$ as defined below; and wherein X is —CONR$^2$—, —CSNR$^2$—, —NR$^{12}$CO—, —NR$^{12}$CS—, —NR$^{12}$CONR$^2$—,

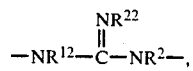

—SO$_2$NR$^2$— or —CO—; or, when $R^1$ is not hydrogen, is —O—, —NR$^2$—, —(NO)R$^2$—, —(PO)R$^2$—, —NR$^{12}$COO—; —NR$^{12}$SO$_2$—, —S—, —SO— or —SO$_2$—; wherein $R^2$ is hydrogen or alkyl or $R^1$ and $R^2$ together form alkylene or halogenoalkylene; wherein $R^{12}$ is hydrogen or alkyl and wherein $R^{22}$ is hydrogen, cyano or nitro; or a salt thereof when appropriate.

8 Claims, No Drawings

STEROID DERIVATIVES

This invention relates to new steroid derivatives which possess antioestrogenic activity.

Various oestradiol derivatives are known which bear a carboxyalkyl substituent at the 7α-position. These have been used, when bound via the carboxy group to polyacrylamide resin or to agarose, for the purification of oestrogen receptors (Journal of Biological Chemistry, 1978, 253, 8221); and, when conjugated with bovine serum albumin, for the preparation of antigens (United Kingdom Specification No. 1,478,356).

We have now found that certain 7α-substituted derivatives of oestradiol and related steroids possess potent antioestrogenic activity.

According to the invention there is provided a steroid derivative of the formula:

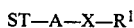

ST—A—X—R$^1$ wherein ST is a 7α-linked steroid nucleus of the general formula:

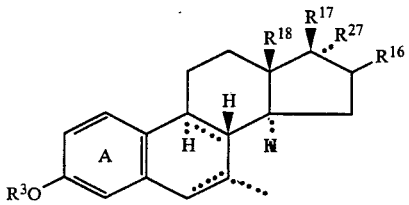

wherein the dotted lines between carbon atoms 6 and 7, and carbon atoms 8 and 9, of the steroid nucleus indicate that there is an optional double bond between carbon atoms 6 and 7, or that there are two optional double bonds between carbon atoms 6 and 7 and carbon atoms 8 and 9;

wherein the aromatic ring A may optionally bear one or two halogen or alkyl substituents;

wherein R$^3$ is hydrogen or alkyl, alkanoyl, alkoxycarbonyl, carboxyalkanoyl or aroyl each of up to 10 carbon atoms;

wherein R$^{16}$ is hydrogen, alkyl of up to 6 carbon atoms which is preferably in the β-configuration, or hydroxy which is preferably in the α-configuration;

wherein either R$^{17}$ (in the β-configuration) is hydroxy or alkanoyloxy, carboxyalkanoyloxy or aroyloxy each of up to 10 carbon atoms; and R$^{27}$ (in the α-configuration) is hydrogen or alkyl, alkenyl or alkynyl each of up to 6 carbon atoms;

or R$^{17}$ and R$^{27}$ together form oxo (=O);

wherein R$^{18}$ is alkyl of up to 6 carbon atoms;

wherein A is straight- or branched-chain alkylene, alkenylene or alkynylene each of from 3 to 14 carbon atoms, which may have one or more hydrogen atoms replaced by fluorine atoms, or has the formula

—A$^1$—Y—A$^{11}$— wherein A$^1$ and A$^{11}$ are each alkylene or alkenylene, optionally flourinated, having together a total of 2 to 13 carbon atoms and Y is —O—, —S—, —SO—, —SO$_2$—, —CO— or —NR— wherein R is hydrogen or alkyl of up to 3 carbon atoms;

or A$^1$ is alkylene or alkenylene, optionally fluorinated, and A$^{11}$ is a direct link or alkylene or alkenylene, optionally fluorinated, such that A$^1$ and A$^{11}$ together have a total of 1 to 12 carbon atoms, and Y is —NR—CO—, —CONR—, —COO—, —OCO— or phenylene wherein R has the meaning stated above;

wherein R$^1$ is hydrogen, or alkyl, alkenyl, cycloalkyl, halogenoalkyl, carboxyalkyl, alkoxycarbonylalkyl, aryl or arylalkyl each of up to 10 carbon atoms, or dialkylaminoalkyl wherein each alkyl is of up to 6 carbon atoms, or R$^1$ is joined to R$^2$ as defined below;

and wherein X is —CONR$^2$—, —CSNR$^2$—, —NR—CO—, —NR—CS—, —NR—CONR$^2$—,

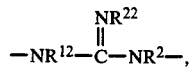

—NR$^{12}$—C—NR$^2$—,

—SO$_2$NR$^2$— or —CO—;

or, when R$^1$ is not hydrogen, is —O—, —NR$^2$—, —(NO)R$^2$—, —(PO)R$^2$—, —NR—COO—, —NR—SO$_2$—, —S—, —SO— or —SO$_2$—;

wherein R$^2$ is hydrogen or alkyl of up to 6 carbon atoms, or R$^1$ and R$^2$ together form alkylene or halogenoalkylene such that, with the adjacent nitrogen atom, they form a heterocyclic ring of 5 to 7 ring atoms, one of which atoms may be a second heterocyclic atom selected from oxygen, sulphur and nitrogen;

wherein R$^{12}$ is hydrogen or alkyl of up to 6 carbon atoms;

and wherein R$^{22}$ is hydrogen, cyano or nitro;

or a salt thereof when appropriate.

A suitable value for the halogen or alkyl substituent in ring A is, for example, fluoro, chloro, bromo, iodo, methyl or ethyl.

A suitable value for R$^3$ when it is alkyl, alkanoyl, alkoxycarbonyl, carboxyalkanoyl or aroyl is, for example, methyl, ethyl, acetyl, propionyl, butyryl, pivalyl, decanoyl, isopropoxycarbonyl, succinyl or benzoyl. R$^3$ is preferably hydrogen or alkanoyl or alkoxycarbonyl each of up to 5 carbon atoms.

A suitable value for R$^{16}$ when it is alkyl is, for example, methyl or ethyl. R$^{16}$ is preferably hydrogen.

A suitable value for R$^{17}$ when it is alkanoyloxy, carboxyalkanoyloxy or aroyloxy is, for example, acetoxy, propionyloxy, succinyloxy or benzoyloxy. R$^{17}$ is preferably hydroxy.

A suitable value for R$^{27}$ when it is alkyl, alkenyl or alkynyl is, for example, ethyl vinyl or ethynyl. R$^{27}$ is preferably hydrogen.

A suitable value for R$^{18}$ is methyl or ethyl, especially methyl.

The group ST— is preferably oestra-1,3,5(10)-triene-3,17β-diol, 3-hydroxyoestra-1,3,5(10)-trien-17-one or 17α-ethynyloestra-1,3,5(10)-triene-3,17β-diol, all of which bear the —A—X—R$^1$ substituent in the 7α-position, or a 3-alkanoyl ester thereof.

One preferred value for the group —A— is a straight-chain alkylene group of the formula

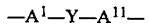

—(CH$_2$)$_n$— wherein n is an integer of from 3 to 14, especially from 7 to 11, which may have one of the hydrogen atoms replaced by fluorine, for example to provide the group —(CH$_2$)$_8$CHFCH$_2$—. A may also be a branched-chain alkylene group, for example the group —(CH$_2$)$_6$CH(CH$_3$)—, or a straight-chain alkenylene group, for example of the formula

—(CH₂)₂CH=CH(CH₂)ₘ— wherein m is an integer from 0 to 10, especially from 3 to 7.

A second preferred value for the group A is a group of the formula

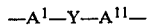—A¹—Y—A¹¹— wherein A¹ is straight-chain alkylene or alkenylene each of 2 to 9 carbon atoms, especially alkylene of 4 to 6 carbon atoms, —Y— is phenylene (ortho, meta- or, especially, para-) and A¹¹ is a direct link, ethylene or vinylene, especially ethylene.

A suitable value for R¹ when it is alkyl, alkenyl or cycloalkyl is, for example, methyl, ethyl, n-propyl, isopropyl, n-butyl, isobutyl, t-butyl, n-pentyl, t-pentyl, 2,2-dimethylpropyl, 1-methylbutyl, 2-methylbutyl, 3-methylbutyl, n-hexyl, 1,1-dimethylbutyl, 1,3-dimethylbutyl, n-heptyl, n-nonyl, n-decyl, n-undecyl, allyl, cyclopentyl or cyclohexyl.

A suitable value for R¹ when it is aryl or arylalkyl is, for example, phenyl, 2-ethylphenyl, p-fluorophenyl, p-chlorophenyl, m-chlorophenyl, p-cyanophenyl, p-methoxyphenyl, benzyl, α-methylbenzyl, p-chlorobenzyl, p-fluorophenethyl or p-chlorophenethyl.

A suitable value for R¹ when it is halogenoalkyl, carboxyalkyl, alkoxycarbonylalkyl or dialkylaminoalkyl is, for example, 2-chloro-2,2-difluoroethyl, 2,2,2-trifluoroethyl, 2,2,3,3,3-pentafluoropropyl, 3-chloropropyl, 2,2-difluorobutyl, 4,4,4-trifluorobutyl, 1H,1H-heptafluorobutyl, 4,4,5,5,5-pentafluoropentyl, 4,4,5,5,6,6,6-heptafluorohexyl, 1H,1H-tridecafluoroheptyl, 5-carboxypentyl, 5-methoxycarbonylpentyl or 3-dimethylaminopropyl.

A suitable value for the heterocyclic ring —NR¹R² is, for example, pyrrolidino, piperidino, 4-methylpiperidino, 4-ethylpiperidino, 3-methylpiperidino, 3,3-dimethylpiperidino, 4-chloropiperidino, morpholino or 4-methylpiperazino.

A suitable value for R² or R¹² when it is alkyl is, for example, methyl, ethyl or n-butyl.

One appropriate salt is an acid-addition salt of a steroid derivative which possesses an amino function, for example a compound wherein Y is —NR—, X is —NR²— or R¹ is dialkylaminoalkyl. A suitable acid-addition salt is, for example, a hydrochloride, hydrobromide, acetate, citrate, oxalate or tartrate.

Another appropriate salt is a base-addition salt of a steroid derivative which possesses a carboxy function, for example a compound wherein R¹ is carboxyalkyl. A suitable base-addition salt is, for example, a sodium, potassium, ammonium or cyclohexylamine salt.

A preferred steroid derivative of the invention has the formula:

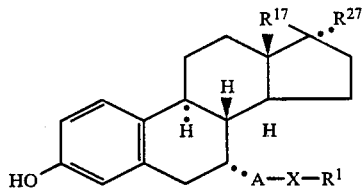

wherein R¹⁷ is hydroxy and R²⁷ is hydrogen or ethynyl, or R¹⁷ and R²⁷ together form oxo;

wherein —A— is —(CH₂)ₙ—, wherein n is an integer from 3 to 14, especially from 7 to 11, or —A— is

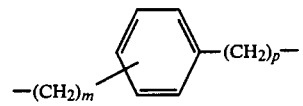

wherein m is an integer from 2 to 9, especially from 4 to 6, and p is 0 to 2, especially 0 or 2; wherein R¹ is alkyl, fluoroalkyl or cycloalkyl each of up to 10 carbon atoms, or phenyl, chlorophenyl or benzyl, or is linked to R² as stated below;

wherein X is —CONR²—, —NR¹²CO—, —S—, —SO— or —SO₂—, wherein R² is hydrogen or alkyl of up to 3 carbon atoms or together with R¹ forms alkylene of 5 or 6 carbon atoms, and wherein R¹² is hydrogen or alkyl of up to 3 carbon atoms.

A particularly preferred steroid derivative of the invention has the last-mentioned formula wherein the number of carbon atoms in the two groups A and R¹ adds up to between 12 and 16, inclusive, especially 14 if neither R¹ nor A contains a phenyl or phenylene group, and 16 if there is a phenylene group in —A— or a phenyl group in R¹.

Specific steroid dervatives of the invention are hereinafter described in the Examples. Of these, particularly preferred compounds are:

N-n-butyl-N-methyl-, N-2,2,3,3,4,4,4-heptafluorobutyl-N-methyl- and N,N-(3-methylpentamethylene)-11-(3,17β-dihydroxyoestra-1,3,5(10)-trien-7α-yl)undecamide;

N-n-butyl- and N-2,2,3,3,4,4,4-heptafluorobutyl-3-p-[4-(3,17β-dihydroxyoestra-1,3,5(10)-trien-7α-yl)butyl]-phenylpropionamide;

7α-(10-p-chlorophenylthiodecyl)-, 7α-(10-p-chlorophenylsulphinyldecyl)-, 7α-[9-(4,4,5,5,5-pentafluoropentylsulphinyl)nonyl]-, 7α-[10-(4,4,4-trifluorobutylsulphinyl)-decyl]- and 7α-[10-(p-chlorobenzylsulphonyl)decyl]oestra-1,3,5(10)-triene-3,17β-diol; and 7α-(9-n-heptylsulphinylnonyl)oestra-1,3,5(10)-triene-3,17β-diol.

A preferred process for the manufacture of a steroid derivative of the invention wherein X has the formula —CONR²—, —CSNR²— or —SO₂NR²— comprises the reaction of a compound of the formula ST¹—A—Z¹, wherein A has the meaning stated above, wherein ST¹ either has the same meaning as stated above for ST, or is an equivalent 7α-linked steroid nucleus which bears one or more protecting groups for functional derivatives, and wherein Z¹ is an activated group derived from a carboxylic, thiocarboxylic or sulphonic acid, with an amine of the formula HNR¹R², wherein R¹ and R² have the meanings stated above, whereafter any protecting group in ST¹ is removed by conventional means.

A suitable activated group Z¹ is, for example, a mixed anhydride, for example an anhydride formed by reaction of the acid with a chloroformate such as isobutyl chloroformate.

A suitable protecting group in ST¹ is, for example, an alkyl or aralkyl ether, for example the methyl or benzyl ether, of the 3-hydroxy function, or a tetrahydropyranyl ether of the 17β-hydroxy function.

A preferred process for the manufacture of a steroid derivative of the invention wherein X has the formula —CO— comprises the reaction of an acid of the formula $ST^1$—A—COOH, wherein $ST^1$ and A have the meanings stated above, with an organometallic compound of the formula $R^1$—M, wherein $R^1$ has the meaning stated above and M is a metal group, for example the lithium group, whereafter any protecting group in $ST^1$ is removed by conventional means.

A preferred process for the manufacture of a steroid derivative of the invention wherein X has the formula —S—, —O—, —$NR^2$— or —$(PO)R^2$— comprises the reaction of a compound of the formula $ST^1$—A—$Z^2$, wherein $ST^1$ and A have the meanings stated above and wherein $Z^2$ is a displaceable group, with a compound of the formula $R^1SH$, $R^1OH$, $HNR^1R^2$ or $R^1R^2P$—$C_6H_5$ wherein $R^1$ and $R^2$ have the meanings stated above, whereafter any protecting group in $ST^1$ is removed by conventional means, and whereafter a phosphonium salt is hydrolysed to the phosphinyl compound.

A suitable value for $Z^2$ is, for example, a halogen atom or a sulphonyloxy group, for example the methanesulphonyloxy or toluene-p-sulphonyloxy group.

A preferred process for the manufacture of a steroid derivative of the invention wherein X has the formula —$NR^{12}CO$—, —$NR^{12}CS$—, —$NR^{12}CONR^2$—,

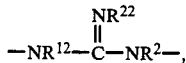

—$NR^{12}COO$— or —$NR^{12}SO_2$— comprises the reaction of a compound of the formula $ST^1$—A—$NHR^{12}$, wherein $ST^1$, A and $R^{12}$ have the meanings stated above, with an acylating agent derived from an acid of the formula $R^1COOH$, $R^1CSOH$, $R^1OCOOH$ or $R^1SO_2OH$; or, for the manufacture of a urea, with an isocyanate of the formula $R^1NCO$; or, for the manufacture of a guanidine, with a cyanamide of the formula $R^1NR^2$—CN, whereafter any protecting group in $ST^1$ is removed by conventional means.

A suitable acylating agent is, for example, an acyl chloride or acyl anhydride.

The starting materials for use in all the abovementioned processes may be obtained by reacting a steroid derivative of the formula

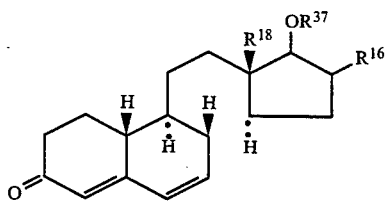

wherein $R^{16}$ and $R^{18}$ have the meanings stated above and wherein $R^{37}$ is an acyl group, for example the acetyl group, with a compound of the formula

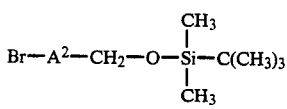

wherein $A^2$ either has the same meaning as stated above for A, or wherein —$A^2$—$CH_2$— has the same meaning as stated above for A; separating the isomers at the 7-position of the steroid nucleus to provide the 7α-isomer; hydrolysing off the dimethyl-t-butylsilyl protecting group; and converting the steroidal part of the molecular to the required structure by conventional reactions. The intermediate product obtained, which has the formula:

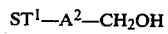

wherein $ST^1$ has the meaning stated above, may be oxidised to the corresponding carboxylic acid of the formula $ST^1$—$A^2$—COOH which provides the starting material for the first or second process of the invention described above;

or it may be converted into a compound of the formula $ST^1$—$A^2$—$CH_2Z^2$ by reaction with a halogenating agent or a sulphonylating agent to provide the starting material for the third process of the invention described above.

The starting material for the fourth process of the invention described above may be obtained by using the third process of the invention described above except that an amine of the formula $R^{12}NH_2$ is used in place of an amine of the formula $HNR^1R^2$.

The intermediate of the formula $ST^1$—$A^2$—$CH_2OH$ may be oxidised to an aldehyde of the formula $ST^1$—$A^2$—CHO which may then be used, by reaction with an appropriately-substituted hydrocarbyltriphenylphosphonium salt or hydrocarbyltriethylphosphonate, to prepare a starting material wherein —A— is alkenylene.

An alternative process for the manufacture of a steroid derivative of the invention wherein —A— is alkenylene of the formula —$A^3$—CH=CH—$A^4$— comprises the reaction of a compound of the formula:

wherein $ST^1$ and $A^3$ have the meanings stated above, with a triphenylphosphonium salt of the formula:

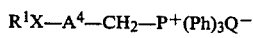

wherein $R^1$, X and $A^4$ have the meanings stated above and wherein $Q^-$ is an anion, for example the bromide ion.

The reaction may be carried out in solution in dimethyl sulphoxide in the presence of dimsyl sodium.

The steroidal aldehyde starting material when —$A^3$— is —$A^2$— as defined above may be obtained by oxidation of the corresponding alcohol as described above. The steroidal aldehyde starting material wherein —$A^3$— is a direct link may be obtained from the 3-keto-$\Delta^{4,6}$-inital steroidal starting material described above by reaction with cyanide to give the 3-keto-$\Delta^4$-7α-cyano compound, aromatisation, suitable protection and then reduction of the cyano group to the formyl group.

The phosphonium starting material may be obtained by reaction of triphenylphosphine with a bromide of the formula

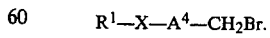

A steroid derivative of the invention wherein ST is a 17β-hydroxy-steroid derivative may be converted by conventional reactions into the corresponding 17-keto steroid derivative, and thence to the corresponding 17β-hydroxy-17α-hydrocarbyl steroid derivative (that is, a steroid derivative of the invention wherein $R^{27}$ is alkyl, alkenyl or alkynyl). Similarly, a steroid derivative of the invention wherein $R^3$ and/or $R^{17}$ are other than hydrogen may be obtained from the corresponding compounds wherein $R^3$ and/or $R^{17}$ are hydrogen by conventional etherification or esterification processes, and these may also be used in reverse to prepare the corresponding hydroxy compounds.

A steroid derivative of the invention wherein A is alkenylene may be hydrogenated to provide the corresponding compound wherein A is alkylene.

A steroid derivative of the invention wherein —X— is —CH$_2$NR$^2$— or —NR$^2$CH$_2$— may be obtained by the reduction, for example with borane, of the corresponding compound wherein —X— is —CONR$^2$— or —NR$^2$CO—.

A steroid derivative of the invention wherein —X— is —CSNH— or —NHCS— may be obtained by the reaction of the corresponding compound wherein X is —CONH— or —NHCO— with 2,4-bis-(4-methoxyphenyl)-1,3-dithia-2,4-diphosphetane-2,4-disulphide.

A steroid derivative of the invention wherein X is —(NO)R$^2$, —SO— or —SO$_2$— may be obtained by the oxidation of the corresponding compound wherein X is —NR$^2$— or —S—. The conditions for the oxidation will be chosen to provide the desired product; for example aqueous sodium metaperiodate will oxidise the sulphur group to sulphinyl, and m-chloroperbenzoic acid in chloroform solution will oxidise the sulphur group to sulphonyl or the amine to its oxide.

As stated above, a steroid derivative of the invention possesses antioestrogenic activity. This may be demonstrated by its effect in antagonising the increase in weight of the uterus of an immature female rat produced by administering oestradiol benzoate to said rat. Thus, when a steroid derivative of the invention and oestradiol benzoate are co-administered for 3 days to such a rat, a smaller increase in uterine weight is produced than the substantial increase which would be produced by the administration of oestradiol benzoate without the steroid derivative of the invention.

In particular, a preferred steroid derivative of the invention produces an antioestrogenic effect at a dose which produces no partial agonist effect, unlike the known antioestrogens tamoxifen and clomiphene. When a preferred steroid is coadministered with oestradiol benzoate to a rat as described above, no increase in uterine weight whatsoever is observed at a suitable dose.

A compound with the above pharmacological properties is of value in the treatment of the same conditions in which tamoxifen is beneficial, in particular, in the treatment of anovulatory infertility and in the treatment of breast tumors. It is also of value in the treatment of menstrual disorders.

When used to produce an anti-oestrogenic effect in warm-blooded animals, a typical daily dose is from 0.1 to 25 mg/kg. administered orally or by injection. In man this is equivalent to an oral dose of from 5 to 1250 mg./day. A steroid derivative of the invention is most conveniently administered to man in the form of a pharmaceutical composition.

According to a further feature of the invention, there is provided a pharmaceutical composition comprising a steroid derivative of the invention together with a pharmaceutically acceptable diluent or carrier.

The composition may be in a form suitable for oral or parenteral administration. A tablet or capsule is a particularly convenient form for oral administration and such a composition may be made by conventional methods and contain conventional excipients. Thus a tablet could contain diluents, for example mannitol or maize starch, disintegrating agents, for example alginic acid, binding agents, for example methyl-cellulose, and lubricating agents, for example magnesium stearate.

The composition may contain, in addition to the steroid derivative of the invention, one or more antiandrogenic agents or antiprogestational agents.

A composition for oral administration may conveniently contain from 5 to 500 mg. of a steroid derivative of the invention.

The invention is illustrated but not limited by the following Examples:

EXAMPLE 1

N-Methylmorpholine (0.24 ml.) and isobutyl chloroformate (0.288 ml.) were successively added to a stirred solution of 11-(17$\beta$-acetoxy-3-benzoyloxyoestra-1,3,5(10)-trien-7$\alpha$-yl)undecanoic acid (1.0 g.) in methylene chloride (17 ml.) which was cooled to $-10°$ C., and after 30 minutes n-butylamine (0.29 ml.) was added and the mixture was stirred at laboratory temperature for 15 minutes. Saturated aqueous sodium bicarbonate solution (20 ml.) was added and the mixture was extracted four times with methylene chloride (50 ml. each time). The combined extracts were washed with water (10 ml.), dried and evaporated to dryness. There was thus obtained as residue 11-(17$\beta$-acetoxy-3-benzoyloxy-N-n-butyloestra-1,3,5(10)-trien-7$\alpha$-yl)undecanamide as an oil.

Aqueous N-sodium hydroxide solution (8 ml.) was added to a stirred solution of the above amide (1.06 g.) in a mixture of methanol (16 ml.) and tetrahydrofuran (8 ml.) and the mixture was stirred at laboratory temperature for 18 hours, neutralised with aqueous N-hydrochloric acid and the organic solvents were removed by evaporation. Water (40 ml.) was added and the mixture was extracted four times with methylene chloride (60 ml. each time). The combined extracts were washed with water (10 ml.), dried and evaporated to dryness and the residue was purified by chromatography on a silica gel (Merck Kieselgel 60) column using a 13:7 v/v mixture of ethyl acetate and toluene as eluant. There was thus obtained N-n-butyl-11-(3,17$\beta$-dihydroxyoestra-1,3,5(10)trien-7$\alpha$-yl)undecanamide as an oil which was characterised by the following data:

| Proton magnetic resonance spectrum (in CDCl$_3$) | | | |
|---|---|---|---|
| Shift ($\delta$) | Type of peak | No of protons | Assignment |
| 7.16 | multiplet | 1 | aromatic protons at positions 1, 2 and 4 |
| 6.65 | " | 2 | |
| 3.7 | | 1 | position 17 |
| 3.28 | quartet | 2 | —CH$_2$— adjacent to —CO— |
| 0.90 | triplet | 3 | —CH$_3$ in n-butyl |
| 0.78 | singlet | 3 | position 18 |

Mass Spectrum

M$^+$=511.4039 (C$_{33}$H$_{53}$O$_3$N requires 511.4024).
M—H$_2$O=493.
M—(CH$_2$CONHC$_4$H$_9$)=397.

Thin layer chromatography (silica gel plates using a 7.3 v/v mixture of ethyl acetate and toluene) $R_F=0.3$.

The 11-(17β-acetoxy-3-benzoyloxyoestra-1,3,5(10)-trien-7α-yl)-undecanoic acid used as starting material was obtained as follows:

A solution of dimethyl-t-butylsilyl chloride (37.3 g.) in tetrahydrofuran (40 ml.) was added to a solution of 11-bromoundecanol (50.18 g.) and imidazole (28.95 g.) in tetrahydrofuran (120 ml.) and the mixture was kept at laboratory temperature for 1.75 hours, diluted with diethyl ether (300 ml.) and filtered. The filtrate was evaporated to dryness and the residue purified by chromatography on silica gel using a 4:1 v/v mixture of petroleum ether (b.p. 60°–80° C.) and toluene as eluant.

A solution of the 11-(dimethyl-t-butylsilyloxy)undecyl bromide thus obtained (73.1 g.) in tetrahydrofuran (200 ml.) was added during 2 hours to a stirred suspension of magnesium turnings (4.8 g.) in tetrahydrofuran (20 ml.) under normal conditions for preparation of a Grignard reagent, and the mixture was heated under reflux for 2 hours, diluted with tetrahydrofuran (100 ml.) and cooled to −30° C. Cuprous iodide (19.05 g., dried at 100° C. immediately before use) was added, the mixture was vigorously stirred for 10 minutes and a solution of 6-dehydro-19-nortestosterone acetate (15.48 g.) in tetrahydrofuran (50 ml.) was added. The mixture was stirred for 40 minutes, acetic acid (12 ml.) was added and the mixture was evaporated to dryness. Water (150 ml.) was added to the residue, and the mixture was extracted four times with diethyl ether (300 ml. each time). The combined extracts were washed with water (50 ml.), dried and evaporated to dryness, and the residue was purified by chromatography on a silica gel column using a 24:1 v/v mixture of toluene and ethyl acetate as eluant.

A mixture of 17β-acetoxy-7α-[11-(dimethyl-t-butylsilyloxy)undecyl]oestr-4-ene-3-one thus obtained (11.2 g.), acetic acid (62 ml.), water (31 ml.) and tetrahydrofuran (56 ml.) was stirred at 50° C. for 2.75 hours and was then evaporated to dryness. A solution of the residue in pyridine (56 ml.) and acetic anhydride (28 ml.) was kept at laboratory temperature for 18 hours, cooled to 0° C., water (10 ml.) was added and the mixture was stirred for 45 minutes and then evaporated to dryness. The residue was dissolved in diethyl ether (400 ml.) and the solution was washed with saturated aqueous sodium bicarbonate solution (20 ml.) and then with water (20 ml.), dried and evaporated to dryness.

A solution of the 17β-acetoxy-7α-(11-acetoxyundecyl)oestr-4-ene-3-one thus obtained (8.98 g.) in acetonitrile (50 ml.) was added rapidly to a vigorously stirred suspension of cupric bromide (7.75 g.) and lithium bromide (1.52 g.) in acetonitrile (120 ml.) which was heated under reflux under an atmosphere of argon, and the mixture was stirred and heated for 30 minutes and then cooled. Saturated aqueous sodium bicarbonate solution (200 ml.) was added and the mixture was extracted four times with ethyl acetate (200 ml. each time). The combined extracts were washed with water (50 ml.), dried and evaporated to dryness, and the residue was purified by chromatography on a silica gel column using a 9:1 v/v mixture of toluene and ethyl acetate as eluant.

Aqueous N-sodium hydroxide solution (8 ml.) was added to a stirred solution of the 17β-acetoxy-7α-(11-acetoxyundecyl)oestra-1,3,5(10)-trien-3-ol thus obtained (2.8 g.) in methanol (54 ml.) and the mixture was stirred at laboratory temperature for 70 minutes, neutralised with aqueous N-hydrochloric acid and the methanol was removed by evaporation. The residue was extracted four times with ethyl acetate (60 ml. each time) and the combined extracts were washed with water (20 ml.), dried and evaporated to dryness. The residue was purified by chromatography on a silica gel column using a 7:3 v/v mixture of toluene and ethyl acetate as eluant.

Aqueous N-sodium hydroxide solution (6 ml.) and benzoyl chloride (0.93 ml.) were added to a stirred solution of the 17β-acetoxy-7α-(11-hydroxy-undecyl)oestra-1,3,5(10)-trien-3-ol thus obtained (1.94 g.) in acetone (20 ml.) which was cooled to 0° C., and the mixture was stirred for 20 minutes and then poured into a mixture of ice-water (200 ml.) and saturated aqueous sodium bicarbonate solution (50 ml.). The mixture was extracted four times with diethyl ether (120 ml. each time) and the combined extracts were washed twice with saturated aqueous sodium bicarbonate solution (15 ml. each time) and then with water (20 ml.), dried and evaporated to dryness. The residue was purified by chromatography on a silica gel column using a 7:3 v/v mixture of toluene and ethyl acetate as eluant.

Jones's reagent (8N-chromic acid solution, 2.3 ml.) was added to a solution of the 17 β-acetoxy-3-benzoyloxy-7α-(11-hydroxyundecyl)oestra-1,3,5(10)-triene thus obtained (2.17 g.) in acetone (37 ml.) which was cooled to 0° C. After 15 minutes isopropanol (0.5 ml.) was added and the mixture was evaporated to dryness. Water (40 ml.) was added and the mixture was extracted three times with methylene chloride (60 ml. each time). The combined extracts were washed twice with water (10 ml. each time), dried and evaporated to dryness, and the residue was purified by chromatography on a silica gel column using a 7:3 v/v mixture of toluene and ethyl acetate as eluant. There was thus obtained 11-(17β-acetoxy-3-benzoyloxyoestra-1,3,5(10)-trien-7α-yl)undecanoic acid.

EXAMPLE 2

The process described in Example 1 was repeated using the appropriate amine in place of n-butylamine. There were thus obtained the compounds described in the following table, all of which were oils the structures of which were confirmed by proton magnetic resonance and mass spectroscopy:

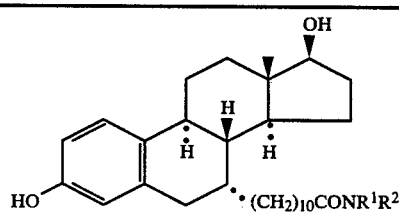

| $R^1$ | $R^2$ | |
|---|---|---|
| H | H | * |
| ethyl | H | |
| n-propyl | H | |
| isopropyl | H | + |
| isobutyl | H | + |
| t-butyl | H | |
| 3-methylbutyl | H | + |
| 1-methylbutyl | H | |
| 2-methylbutyl | H | + |
| 2,2-dimethylpropyl | H | |
| n-hexyl | H | |

-continued

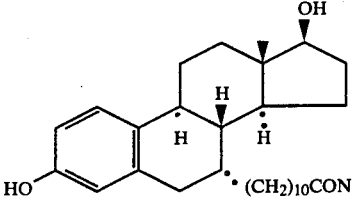

| $R^1$ | $R^2$ | |
|---|---|---|
| 1,1-dimethylbutyl | H | + |
| 1,3-dimethylbutyl | H | |
| cyclohexyl | H | |
| 2,2,2-trifluoroethyl | H | |
| 2,2,3,3,4,4,4-heptafluorobutyl | H | + |
| 2,2-difluorobutyl | H | |
| 3-chloropropyl | H | |
| phenyl | H | |
| 4-methoxyphenyl | H | |
| 4-chlorophenyl | H | + |
| 4-cyanophenyl | H | |
| 2-ethylphenyl | H | |
| benzyl | H | |
| 1-phenylethyl | H | |
| 5-carboxypentyl | H | ** |
| 3-dimethylaminopropyl | H | |
| n-butyl | methyl | |
| 2,2-dimethylpropyl | methyl | |
| 2-methylbutyl | methyl | |
| n-hexyl | methyl | |
| 2,2,3,3,3-pentafluoropropyl | methyl | |
| 2,2-difluorobutyl | methyl | |
| 4,4,4-trifluorobutyl | methyl | |
| 2,2,3,3,4,4,4-heptafluorobutyl | methyl | + |
| benzyl | methyl | |
| n-butyl | ethyl | |
| n-butyl | n-butyl | |
| 2,2,2-trifluoroethyl | n-butyl | |
| —(CH$_2$)$_5$— | | |
| —(CH$_2$)$_2$—N—(CH$_2$)$_2$—<br>               \|<br>               CH$_3$ | | |
| —(CH$_2$)$_2$CH(CH$_2$)$_2$—<br>         \|<br>         CH$_3$ | | + |
| —CH$_2$CH(CH$_2$)$_3$—<br>       \|<br>       CH$_3$ | | + |
| —(CH$_2$)$_2$CHCl(CH$_2$)$_2$— | | |
| —(CH$_2$)$_2$CH(CH$_2$)$_2$—<br>         \|<br>         C$_2$H$_5$ | | |
|            CH$_3$<br>           \|<br>—(CH$_2$)$_3$C—CH$_2$—<br>           \|<br>           CH$_3$ | | |

*A solution of ammonia in tetrahydrofuran was used as starting material.
**Methyl 6-aminohexanoate was used as starting material, the methyl ester being hydrolysed during the second stage of the process.

In some cases (indicated + in the above table) the undecanoic acid used as starting material was the 3-hydroxy- rather than the 3-benzoyloxy-compound, which was prepared by a shortened route as follows:

The 17β-acetoxy-7α-(11-acetoxyundecyl)oestr-4-ene-3-one, prepared as described in the 5th paragraph of Example 1, was hydrolysed to the corresponding 11-hydroxyundecyl compound as described in the 7th paragraph of Example 1, and this product was purified by chromatography on a silica gel column using a 3:2 v/v mixture of toluene and ethyl acetate as eluant. It was then oxidised to the corresponding undecanoic acid as described in the 9th paragraph of Example 1, and this product was purified by chromatography on a silica gel column using a 19:1 v/v mixture of methylene chloride and methanol as eluant. The undecanoic acid was aromatised as described in the 6th paragraph of Example 1, except that the pH of the reaction mixture was adjusted to 3 before extraction into ethyl acetate. The product was purified by chromatography on a silica gel column using a 3:1 v/v mixture of diethyl ether and petroleum ether (b.p. 60°–80° C.) as eluant. There was thus obtained, as an oil, 11-(17β-acetoxy-3-hydroxyoestra-1,3,5(10)-trien-7α-yl)undecanoic acid.

EXAMPLE 3

The process described in Example 1 was repeated except that the appropriate (17β-acetoxy-3-hydroxyoestra-1,3,5-(10)trien-7α-yl)alkenoic acid and the appropriate amine were used as starting materials. There were thus obtained the compounds described in the following table, all of which were oils the structures of which were confirmed by proton magnetic resonance and mass spectroscopy:

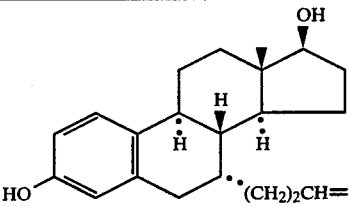

| m | $R^1$ | $R^2$ |
|---|---|---|
| 3 | n-butyl | H |
| 3 | n-heptyl | H |
| 3 | n-heptyl | methyl |
| 5 | n-butyl | H |
| 5 | n-pentyl | H |
| 8 | ethyl | H |
| 8 | n-butyl | H |
| 10 | methyl | methyl |

The initial compounds obtained are (17β-acetoxy-3-isobutyloxycarbonyloestra-1,3,5(10)-trien-7α-yl)alkenamides, the hydroxy group at the 3-position being converted into the carbonate during the first stage of the amide-forming reaction by the isobutyl chloroformate.

The alkenoic acids used as starting materials were prepared by a process exemplified by the following preparation of 8-(17β-acetoxy-3-hydroxy-oestra-1,3,5(10)-trien-7α-yl)octa-5-enoic acid:

The process described in the first paragraph of Example 1 relating to the preparation of starting materials was repeated except that dimethyl-t-butylsilyl chloride was reacted with 3-bromopropanol instead of 11-bromoundecanol. The Grignard reagent from this was reacted with 6-dehydro-19-nortestosterone, and the sequence of reactions described in the succeeding five paragraphs of Example 1 was repeated. There was thus obtained 17β-acetoxy-3-benzoyloxy-7α-(3-hydroxypropyl)oestra-1,3,5(10)-triene.

Pyridinium chlorochromate (0.427 g.) was added to a stirred solution of this oestratriene (0.629 g.) in methylene chloride (13 m.) and the mixture was stirred for 2 hours, diluted with diethyl ether (50 ml.) and filtered through a filter-aid. The filtrate was evaporated to dryness and the residue was purified by chromatography on a silica gel column using a 19:1 v/v mixture of toluene and ethyl acetate as eluant. There was thus obtained 3-(17β-acetoxy-3-benzoyloxyoestra-1,3,5(10)-trien-7α-yl)propionaldehyde.

Finely powdered (4-carboxybutyl)triphenylphosphonium bromide (1.4 g.) was degassed by heating in vacuo at 100° C. for 1 hour and was then dissolved in dimethyl-sulphoxide (5 ml.) under an atmosphere of a nitrogen. A 2-molar solution of methanesulphinylmethyl sodium in dimethyl sulphoxide (3.8 ml.) was added dropwise, and a solution of the above aldehyde (0.25 g.) in toluene (2 ml.) was then added. The mixture was stirred for 1 hour and then evaporated to dryness under reduced pressure at a temperature not exceeding 40° C. The residue was shaken with water (5 ml.) and diethyl ether (10 ml.) and the aqueous solution was separated, acidified to pH 3.5 with aqueous 2N-oxalic acid solution and extracted four times with ethyl acetate (10 ml. each time). The combined extracts were washed with water, dried and evaporated to dryness and the residue was purified by chromatography on a silica gel column using a 1:1 v/v mixture of toluene and ethyl acetate as eluant. There was thus obtained 8-(17β-acetoxy-3-hydroxyoestra-1,3,5(10)-trien-7α-yl)octa-5-enoic acid.

The corresponding deca-7-enoic, trideca-10-enoic and pentadeca-12-enoic acids were obtained by using (6-carboxyhexyl)-, (9-carboxynonyl)- or (11-carboxyundecyl)triphenylphosphonium bromide in place of (4-carboxybutyl)triphenylphosphonium bromide.

EXAMPLE 4

5% Palladium-on-charcoal catalyst (0.025 g.) was added to a solution of N-n-butyl-8-(3,17β-dihydroxyoestra-1,3,5(10)-trien-7α-yl)oct-5-enamide (Example 3; 0.05 g.) in ethyl acetate (2.5 ml.) and the mixture was stirred at laboratory temperature under an atmosphere of hydrogen for 1 hour and then filtered. The filtrate was evaporated to dryness and there was thus obtained as oily residue N-n-butyl-8-(3,17β-dihydroxyoestra-1,3,5(10)-trien-7α-yl)octanamide, the structure of which was confirmed by spectroscopic means.

The process described above was repeated using the appropriate alkenamide described in Example 3 and there were thus obtained as oils the compounds described in the following table, the structures of all of which were confirmed by spectroscopic means;

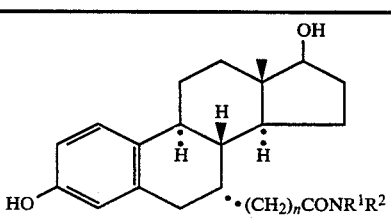

| n | $R^1$ | $R^2$ |
|---|---|---|
| 7 | n-heptyl | H |
| 7 | n-heptyl | methyl |
| 9 | n-butyl | H |
| 9 | n-pentyl | H |
| 12 | ethyl | H |
| 12 | n-butyl | H |
| 14 | methyl | methyl |

EXAMPLE 5

The process described in Example 1 was repeated except that either 3,17β-dihydroxyoestra-1,3,5(10)-trien-7α-yl)pent-2-enoic acid or 3,17β-dihydroxyoestra-1,3,5(10)-trien-7α-yl)pentanoic acid, and the appropriate amine, were used as starting materials. There were thus obtained as oils the compounds described in the following tables, the structures of which were confirmed by proton magnetic resonace and mass spectoscopy.

TABLE I

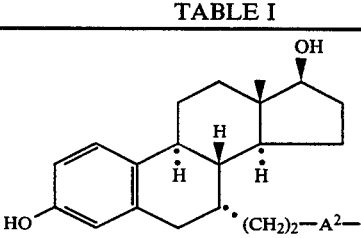

| $A^2$ | $R^1$ | $R^2$ |
|---|---|---|
| —CH₂CH₂— | n-decyl | H |
| —CH₂CH₂— | n-decyl | methyl |
| —CH=CH— | n-decyl | H |

TABLE 2

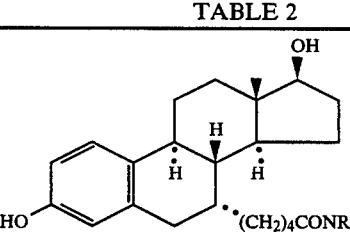

| R | A | $R^1$ | $R^2$ |
|---|---|---|---|
| H | CH₂ | n-heptyl | H |
| H | (CH₂)₂ | n-hexyl | H |
| H | (CH₂)₃ | n-hexyl | H |
| methyl | (CH₂)₃ | n-hexyl | H |
| methyl | (CH₂)₃ | n-hexyl | methyl |

The pentenoic and pentanoic acids used as starting materials were obtained as follows:

Sodium hydride (0.069 g.) was added to a stirred solution of triethylphosphonoacetate (0.413 g.) in tetrahydrofuran (10 ml.) which was maintained at 0° C., and the mixture was stirred at that temperature for 1 hour. A solution of 3-(17β-acetoxy-3-benzoyloxyoestra-1,3,5(10)-trien-7α-yl)propionaldehyde (Example 3, second paragraph relating to preparation of starting materials, 0.25 g.) in tetrahydrofuran (5 ml.) was added and the mixture was stirred at laboratory temperature for 30 minutes, neutralised with acetic acid and evaporated to dryness. The residue was shaken with water (15 ml.), the mixture was extracted three times with ethyl acetate (30 ml. each time) and the combined extracts were washed with water, dried and evaporated to dryness. There was thus obtained as residue ethyl 5-(17β-acetoxy-3-benzoyloxy-oestra-1,3,5(10-trien-7α-yl)pent-2-enoate. Part of this was hydrolysed to the corresponding pent-2-enoic acid with aqueous sodium hydroxide solution for use as one starting material, and part of it was hydrogenated by a similar process to that described in Example 4, and the ethyl 5-(17β-acetoxy-3-benzoyloxyoestra-1,3,5(10)-trien-7α-yl)pentenoate thus obtained was hydrolysed to the corresponding dihydroxypentanoic acid with aqueous sodium hydroxide solution for use as the other starting material.

The amidoalkylamines used as starting materials for the compounds described in Table 2 were obtained as follows:

N-n-Hexyl-4-methylaminobutyramide

A solution of 1-methylpyrrolidin-2-one (5 g.) in aqueous 6N-sodium hydroxide solution (50 ml.) containing methanol (0.1 ml.) was heated under reflux for 3 hours, cooled to 0° C. and benzyl chloroformate (9.5 g.) was added dropwise. The mixture was kept at 0° C. for 12 hours and then poured onto a mixture of equal volumes of ice and concentrated aqueous hydrochloric acid. The mixture was extracted with ethyl acetate and the extract was washed with water, dried and evaporated to dryness.

Triethylamine (3.7 ml.) and ethyl chloroformate (2.5 ml.) were successively added to a stirred solution of the 4-(N-benzyloxycarbonyl-N-methylamino)butyric acid thus obtained (6.0 g.) in ethyl acetate (100 ml.) which was cooled to −20° C., and the mixture was stirred at that temperature for 15 minutes. A solution of n-hexylamine (3.2 ml.) in ethyl acetate (30 ml.) was added and the mixture was allowed to warm up to laboratory temperature and stirred at that temperature for 16 hours, then washed successively with dilute aqueous hydrochloric acid, saturated aqueous sodium bicarbonate solution and saturated aqueous sodium chloride solution, dried and evaporated to dryness.

A solution of the 4-(N-benzyloxycarbonyl-N-methylamino)-N-n-hexylbutyramide thus obtained (6.6 g.) in ethanol (100 ml.) was shaken with hydrogen in the presence of a 10% palladium-on-charcoal catalyst (0.6 g.) for 18 hours, filtered and evaporated to dryness. There was thus obtained as residual oil N-n-hexyl-4-methylaminobutyramide.

N-n-Hexyl-N-methyl-4-methylaminobutyramide

As above but using N-n-hexyl-N-methylamine in place of n-hexylamine.

Glycine N-n-heptylamide

As above from glycine and benzyl chloroformate (N-benzyloxycarbonylglycine has m.p. 119°–121° C.), then triethylamine, ethyl chloroformate and n-heptylamine.

β-Alanine N-n-hexylamide

As above using β-alanine in place of glycine and n-hexylamine in place of n-heptylamine.

N-n-hexyl-4-aminobutyramide

As above using 4-aminobutyric acid in place of glycine and n-hexylamine in place of n-heptylamine.

EXAMPLE 6

N-Methylmorpholine (0.028 ml.) and isobutyl chloroformate (0.038 ml.) were successively added to a stirred solution of 11-(3-benzyloxy-17β-hydroxyoestra-1,3,5(10)-trien-7α-yl)undec-10-enoic acid (0.109 g.) in tetrahydrofuran (3 ml.) which was cooled to −10° C. The mixture was stirred at −10° C. for 30 minutes, N-methylisobutylamine (0.05 ml.) was added and the mixture was stirred at laboratory temperature for 2 hours. Saturated aqueous sodium bicarbonate solution (5 ml.) was added and the mixture was extracted 3 times with methylene chloride (10 ml. each time). The combined extracts were washed with water (2 ml.), dried and evaporated to dryness, and there was thus obtained as oily residue N-isobutyl-N-methyl-11-(3-benzyloxy-17β-hydroxyoestra-1,3,5(10)-trien-7αyl)undec-10-enamide.

A 10% palladium-on-charcoal catalyst (0.03 g.) was added to a solution of the above compound (0.105 g.) in ethyl acetate (10 ml.) and the mixture was stirred at laboratory temperature under an atmosphere of hydrogen for 5 hours, and then filtered. The filtrate was evaporated to dryness and there was thus obtained as oily residue N-isobutyl-N-methyl-11-(3,17β-dihydroxyoestra-1,3,5(10)-trien-7α-yl)undecanamide, the structure of which was confirmed by proton magnetic resonance spectroscopy and elemental analysis.

The undecenoic acid used as starting material was obtained as follows:

Diethyl aluminium cyanide (100 ml. of a 1.2 molar solution in toluene) was added to a stirred solution of 6-dehydro-19-nortestosterone acetate (9 g.) in tetrahydrofuran (400 ml.) and the mixture was stirred at laboratory temperature for 1 hour and then poured into a mixture of ice (1000 ml.) and aqueous 2N-sodium hydroxide solution (500 m.). The mixture was extracted 3 times with methylene chloride (300 ml. each time) and the combined extracts were washed with water (100 ml.), dried and evaporated to dryness. The residue was stirred with petroleum ether (b.p. 40°–60° C.; 100 ml.) and there was thus obtained 17β-acetoxy-7α-cyano-oestr-4-ene-3-one, m.p. 183°–186° C.

A solution of the above compound (3.38 g.) in acetonitrile (15 ml.) was added rapidly to a vigorously stirred suspension of cupric bromide (4.46 g.) and lithium bromide (0.85 g.) in acetonitrile (30 ml.) which was heated under reflux under an atmosphere of argon. The mixture was stirred and heated under reflux for 10 minutes and then cooled, and saturated aqueous sodium bicarbonate solution (50 ml.) was added. The mixture was extracted 3 times with ethyl acetate (50 ml. each time) and the combined extracts were washed with water (20 ml.), dried and evaporated to dryness. The residue was purified by chromatography on a silica gel column using a 17:3 v/v mixture of toluene and ethyl acetate as eluant, and there was thus obtained 17β-acetoxy-7α-cyanooestra-1,3,5(10)-trien-3-ol. Early fractions eluted from the column contained 17β-acetoxy-6-bromo-7α-cyano-oestra-1,3,5(10)-trien-3-ol which was used in Example 22.

A stirred mixture of the above compound (0.69 g.), benzyl bromide (0.29 ml.), potassium carbonate (0.325 g.) and acetone (20 ml.) was heated under reflux for 16 hours, cooled and filtered and the filtrate was evaporated to dryness. The residue was purified by chromatography on a silica gel column using a 9:1 v/v mixture of toluene and ethyl acetate as eluant, and there was thus obtained 17β-acetoxy-3-benzyloxy-7α-cyano-oestra-1,3,5(10)-triene.

Diisobutyl aluminium hydride (3.1 ml. of a 1.5 molar solution in toluene) was added to a stirred solution of the above compound (0.68 g.) in toluene (10 ml.) and the mixture was stirred at laboratory temperature for 150 minutes. Methanol (2 ml.) and then aqueous 2N-hydrochloric acid (5 ml.) were added and the mixture was stirred for 15 minutes and then extracted three times with ethyl acetate (10 ml. each time). The combined extracts were washed with water (5 ml.), dried and evaporated to dryness. The residue was purified by chromatography on a silica gel column using a 4:1 v/v mixture of toluene and ethyl acetate as eluant. There was thus obtained 3-benzyloxy-17β-hydroxyoestra-1,3,5(10)-triene-7α-carboxaldehyde.

Dimsyl sodium (4 ml. of a 2-molar solution in dimethyl sulphoxide) was added dropwise to a solution of finely powdered (9-carboxynonyl)triphenylphosphonium bromide (1.94 g.) in dimethyl sulphoxide (10 ml.) which was maintained under an atmosphere of nitrogen, and a solution of the above aldehyde (0.3 g.) in a mixture of toluene (2 ml.) and dimethyl sulphoxide (2 ml.) was then added. The mixture was stirred at laboratory temperature for 1 hour and then evaporated to dryness under reduced pressure, and the residue was shaken with water (5 ml.) and diethyl ether (5 ml.). The aqueous solution was separated, acidified to pH 3 with aqueous 2N-oxalic acid solution and extracted three times with diethyl ether (10 ml. each time). The combined extracts were washed with water, dried and evaporated to dryness and the residue was purified by chromatography on a silica gel column using an 11:9 v/v mixture of toluene and ethyl acetate as eluant. There was thus obtained 11-(3-benzyloxy-17β-hydroxyoestra-1,3,5(10)-trien-7α-yl)undec-10-enoic acid.

EXAMPLE 7

The process described in Example 6 was repeated using the appropriate ω-(3-benzyloxy-17β-hydroxyoestra-1,3,5(10)-trien-7α-yl)alkenoic acid and the appropriate amine as starting materials. There were thus obtained the compounds described in the following table, all of which were oils the structures of which were confirmed by proton magnetic resonance and mass spectroscopy:

| A | $R^1$ | $R^2$ |
|---|---|---|
| —(CH$_2$)$_{11}$— | n-propyl | H |
| —(CH$_2$)$_{11}$— | n-butyl | methyl |
| —(CH$_2$)$_{10}$— | 1-methylbutyl | methyl |
| —(CH$_2$)$_{10}$— | cyclopentyl | H |
| —(CH$_2$)$_9$— | 1H,1H,heptafluorobutyl | methyl |
| —(CH$_2$)$_8$— | n-hexyl | methyl |
| —(CH$_2$)$_6$CH(CH$_3$)— | n-butyl | methyl |
| —(CH$_2$)$_6$CH(CH$_3$)— | n-heptyl | H |
| —(CH$_2$)$_7$— | —CH$_2$(CF$_2$)$_5$CF$_3$ | H |
| —(CH$_2$)$_8$CHFCH$_2$— | n-butyl | methyl* |

*In the starting material —A— is —CH=CH—(CH$_2$)$_6$—CF=CH—.

The steroidal starting materials were prepared as described in the second part of Example 6 except that the appropriate (ω-carboxyalkyl)triphenylphosphonium bromide was used as intermediate. The starting material for the last-mentioned compound, marked with an asterisk*, is unusual in that during the reaction of the steroidal-7α-carboxaldehyde with (9-carboxy-8,8-difluorononyl)triphenylphosphonium bromide a molecule of hydrogen fluoride is eliminated and the starting material is the steroidal-7α-yl-3-fluoroundeca-2,10-dienoic acid.

The (9-carboxy-8,8-difluorononyl)triphenylphosphonium bromide used as intermediate was obtained as follows:

A solution of 8-bromooctanoyl chloride (1.2 g.) in methylene chloride (5 ml.) was added to a stirred solution of 2,2-dimethyl-1,3-dioxane-4,6-dione (0.72 g.) and pyridine (0.8 ml.) in methylene chloride (20 ml.) which was kept at 5° C., and the mixture was stirred at that temperature for 1 hour and then at laboratory temperature for 90 minutes, washed successively with aqueous N-hydrochloric acid (20 ml.) and water (20 ml.), dried and evaporated to dryness. The residue was heated under reflux with methanol (20 ml.) for 16 hours, the excess of methanol was removed by evaporation and the residue was distilled under reduced pressure. There was thus obtained methyl 10-bromo-3-oxodecanoate, b.p. 135°–144° C./1 mm.Hg.

A mixture of the above ester (4.4 g.) and sulphur tetrafluoride (10 g.) was heated at 60° C. for 6 hours in a sealed bomb (Hastelloy C) and the resulting tar was extracted with methylene chloride (150 ml.). The extract was washed with saturated aqueous sodium carbonate solution (50 ml.) and then with water (20 ml.), dried and evaporated to dryness. The residue was distilled under reduced pressure and there was thus obtained methyl 10-bromo-3,3-difluorodecanoate, b.p. 175° C./0.2 mm.Hg.

A mixture of the above ester (1.1 g.), acetic acid (1 ml.) and 48% aqueous hydrobromic acid (1 ml.) was heated under reflux for 2 hours and then poured into ice-water (20 ml.). The mixture was extracted three times with ethyl acetate (10 ml. each time) and the combined extracts were washed with water, dried and evaporated to dryness. The residue was distilled under reduced pressure and there was thus obtained 10-bromo-3,3-difluorodecanoic acid, b.p. 200° C./0.15 mm.Hg.

Triphenylphosphine (0.565 g.) was added to a solution of the above acid (0.61 g.) in acetonitrile (5 ml.) and the mixture ws heated under reflux for 18 hours and then evaporated to dryness. There was thus obtained as residual oil (9-carboxy-8,8-difluorononyl)triphenylphosphonium bromide which was used without further purification.

EXAMPLE 8

N-Methylmorpholine (0.107 ml.) and isobutyl chloroformate (0.133 ml.) were successively added to a stirred solution of p-[4-(17β-hydroxy-3-methoxyoestra-1,3,5(10)-trien-7α-yl)but-1-enyl]cinnamic acid (0.17 g.) in methylene chloride (10 ml.) which was cooled to −30° C. under an atmosphere of argon, and the mixture was allowed to warm up to laboratory temperature. n-Hexylamine (0.06 ml.) was added, the mixture was stirred at laboratory temperature for 30 minutes, aqueous 2N-hydrochloric acid (10 ml.) was added and the mixture was extracted three times with diethyl ether (20 ml. each time). The combined extracts were washed with water, dried over magnesium sulphate and evaporated to dryness under reduced pressure. There was thus obtained, as an oil, N-n-hexyl-p-[4-(17β-hydroxy-3-methoxyoestra-1,3,5(10)-trien-7α-yl)but-1-enyl]cinnamide, the structure of which was confirmed by proton magnetic resonance spectroscopy and mass spectroscopy.

Boron tribromide (0.5 ml.) was added to a stirred solution of the above amide (0.12 g.) in methylene chloride (10 ml.) which was cooled to −78° C. under an atmosphere of argon, and the mixture was allowed to warm up to −10° C. and was kept at that temperature for 4 hours. Saturated aqueous sodium bicarbonate solution (10 ml.) was added, the mixture was extracted three times with methylene chloride (15 ml. each time) and the combined extracts were washed with water, dried over magnesium sulphate and evaporated to dryness. There was thus obtained, as an oil, p-[4-(3,17β-dihydroxyoestra-1,3,5(10)-trien-7α-yl)but-1-enyl]-N-n-hexyl-cinnamide, the structure of which was confirmed by nuclear magnetic resonance and mass spectroscopy.

The cinnamic acid used as starting material was obtained as follows:

The process described in the first paragraph of Example 1 relating to the preparation of starting materials was repeated except that dimethyl-t-butylsilyl chloride was reacted with 3-bromopropanol instead of 11-bromoundecanol. The Grignard reagent from this was reacted with 6-dehydro-19-nortestosterone, and the sequence of reactions described in the succeeding two paragraphs of Example 1 was repeated. There was thus obtained 17β-acetoxy-17α-(3-acetoxypropyl)-oestra-1,3,5(10)-trien-3-ol.

Methyl iodide (6 ml.) and potassium carbonate (6 g.) were added to a stirred solution of the above diacetate (5 g.) in acetone (80 ml.), and the mixture was stirred and heated under reflux for 16 hours, cooled and filtered and the filtrate was evaporated to dryness. A solution of the residual 17β-acetoxy-7α-(3-acetoxypropyl)-3-methoxyoestra-1,3,5(10)-triene (4.7 g.) in methanol (50 ml.) was cooled to 0° C., potassium carbonate (2.5 g.) was added and the mixture was stirred at 0° C. for 3 hours and then filtered. The filtrate was evaporated to dryness and the residue was purified by chromatography on a silica gel column (Merck 9385) using a 4:1 v/v mixture of toluene and ethyl acetate as eluant. There was thus obtained 17β-acetoxy-7α-(3-hydroxypropyl)-3-methoxyoestra-1,3,5(10)-triene as an oil.

Pyridinium chlorochromate (3.6 g.) was added to a stirred solution of this oestratriene (3.2 g.) in methylene chloride (100 ml.) and the mixture was stirred for 2 hours and then filtered. The filtrate was evaporated to dryness and the residue was purified by chromatography on a silica gel column (Merck 9385) using a 9:1 v/v mixture of toluene and ethyl acetate as eluant. There was thus obtained 3-(17β-acetoxy-3-methoxyoestra-1,3,5(10)-trien-7α-yl)propionaldehyde.

n-Butyl-lithium (0.67 ml. of a 1.5 molar solution in hexane) was added to a stirred solution of diisopropylamine (0.14 ml.) in tetrahydrofuran (30 ml.) which was cooled to 0° C. under an atmosphere of argon. After 10 minutes the mixture was cooled to −78° C. and a solution of ethyl p-(diethylphosphonylmethyl)cinnamate (0.33 g.; b.p. 175° C./15 mm.Hg; prepared by heating ethyl p-bromomethylcinnamate with triethylphosphite at 120° C. for 2 hours) in tetrahydrofuran (2 ml.) was added dropwise. A solution of the above propionaldehyde (0.19 g.) in tetrahydrofuran (1 ml.) was added and the mixture was allowed to warm up to laboratory temperature and was stirred at the temperature for 16 hours. Aqueous 2N-hydrochloric acid was added and the mixture was extracted three times with diethyl ether (15 ml. each time). The combined extracts were washed with water (20 ml.) and then with saturated aqueous sodium chloride solution (20 ml.), dried over magnesium sulphate and evaporated to dryness. The residue was purified by chromatography on a silica gel column (Merck 9385) using a 17:3 v/v mixture of toluene and ethyl acetate as eluant. There was thus obtained ethyl p-[4-(17β-acetoxy-3-methoxyoestra-1,3,5(10)-trien-7α-yl)but-1-enyl]cinnamate.

Aqueous 2N-sodium hydroxide solution (1 ml.) was added to a stirred solution of the above cinnamate (0.2 g.) in a mixture of methanol (1 ml.) and tetrahydrofuran (1 ml.), and the mixture was stirred at laboratory temperature for 3 hours, acidified with aqueous 2N-hydrochloric acid (2 ml.) and extracted three times with ethyl acetate (10 ml. each time). The combined extracts were washed with water, dried over magnesium sulphate and evaporated to dryness. There was thus obtained as residual gum p-[4-(17β-hydroxy-3-methoxyoestra-1,3,5(10)-trien-7α-yl)but-1-enyl]cinnamic acid.

EXAMPLE 9

A solution of p-[4-(4-(3,17β-dihydroxyoestra-1,3,5(10)-trien-7α-yl)but-1-enyl]-N-n-hexylcinnamide (Example 8; 0.05 g.) in a mixture of ethyl acetate (10 ml.) and ethanol (2 ml.) was stirred with a 20% palladium-on-charcoal catalyst (0.01 g.) under an atmosphere of hydrogen at laboratory temperature and atmospheric pressure for 2 hours, and the mixture was then filtered and evaporated to dryness. There was thus obtained 3-p-[4-(3,17β-dihydroxyoestra-1,3,5(10)-trien-7α-yl)butyl]phenyl-N-n-hexylpropionamide, the structure of which was confined by proton magnetic resonance and mass spectroscopy.

EXAMPLE 10

The processes described in Examples 8 and 9 were repeated using the appropriate amine in place of n-hexylamine as starting material in Example 8. There were thus obtained the compounds described in the following table, all of which were oils the structures of which were confirmed by proton magnetic resonance and mass spectroscopy:

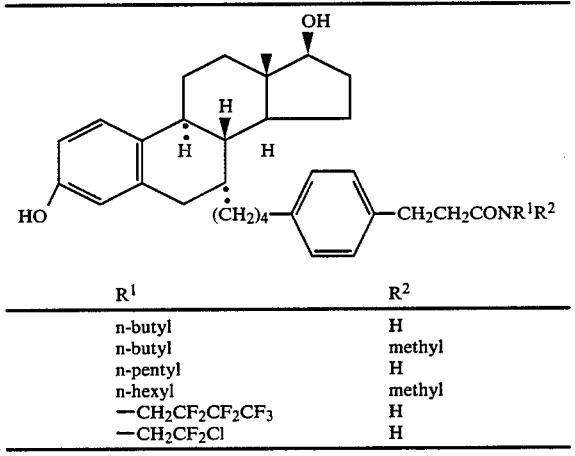

| R¹ | R² |
|---|---|
| n-butyl | H |
| n-butyl | methyl |
| n-pentyl | H |
| n-hexyl | methyl |
| —CH₂CF₂CF₂CF₃ | H |
| —CH₂CF₂Cl | H |

EXAMPLE 11

The process described in Example 8 was repeated using the appropriate amine and the appropriate ω-(17β-hydroxy-3-methoxyoestra-1,3,5(10)-trien-7α-yl)alk-1-enylcinnamic acid or benzoic acid as starting materials. There were thus obtained the compounds described in the following table, all of which were oils the structures of which were confirmed by proton magnetic resonance and mass spectroscopy:

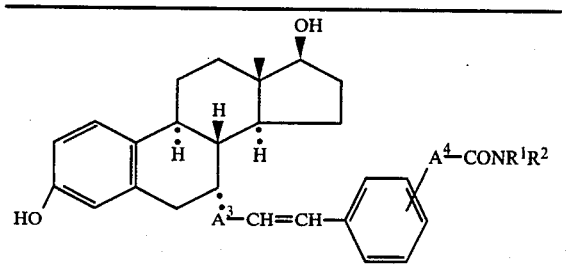

| A³ | Position in benzene ring | A⁴ | R¹ | R² |
|---|---|---|---|---|
| —(CH₂)₂— | meta | — | n-hexyl | H |
| —(CH₂)₂— | meta | —CH=CH— | n-hexyl | H |
| —(CH₂)₄— | para | —CH=CH— | n-butyl | H |
| —(CH₂)₄— | para | —CH=CH— | n-butyl | methyl |
| —(CH₂)₄— | para | — | n-pentyl | H |
| —(CH₂)₄— | para | — | n-hexyl | H |
| —(CH₂)₄— | ortho | — | n-hexyl | H |

The steroidal starting material wherein A³ is —(CH₂)₄— was prepared by a similar process to that described in Example 8 except that in the third paragraph thereof 5-bromopentanol was used in place of 3-bromopropanol. The phosphonate intermediates were prepared from the appropriate ethyl bromomethylcinnamate or ethyl bromomethylbenzoate and triethylphosphite.

EXAMPLE 12

The hydrogenation described in Example 9 was repeated using the appropriate unsaturated compound, described in Example 11, as starting material. There were thus obtained the compounds described in the following table, all of which were oils the structures of which were confirmed by proton magnetic resonance and mass spectroscopy:

| A³ | Position in benzene ring | A⁴ | R¹ | R² |
|---|---|---|---|---|
| —(CH₂)₄— | meta | — | n-hexyl | H |
| —(CH₂)₄— | meta | —CH₂CH₂— | n-hexyl | H |
| —(CH₂)₆— | para | —CH₂CH₂— | n-butyl | H |
| —(CH₂)₆— | para | —CH₂CH₂— | n-butyl | methyl |
| —(CH₂)₆— | para | — | n-pentyl | H |
| —(CH₂)₆— | para | — | n-hexyl | H |
| —(CH₂)₆— | ortho | — | n-hexyl | H |

EXAMPLE 13

The process described in Example 8 was repeated using p-[2-(3-benzyloxy-17β-hydroxyoestra-1,3,5(10)-trien-7α-yl)ethenyl]cinnamic acid and n-octylamine as starting materials. There was thus obtained, as an oil p-[2-(3-benzyloxy-17β-hydroxyoestra-1,3,5(10)-trien-7α-yl)ethenyl]-N-n-octylcinnamide.

The hydrogenation process described in the second paragraph of Example 6 was repeated using the above compound as starting material, and there was thus obtained as an oil 3-p-[2-(3,17β-dihydroxyoestra-1,3,5(10)-trien-7α-yl)ethyl]phenyl-N-n-octylpropionamide, the structure of which was confirmed by proton magnetic resonance and mass spectroscopy.

The cinnamic acid used as starting material was obtained from 3-benzyloxy-17β-hydroxyoestra-1,3,5(10)-trien-7α-carboxaldehyde (described in the sixth paragraph of Example 6) and ethyl p-(deithylphosphonylmethyl)cinnamate by a similar process to that described in the sixth and seventh paragraphs of Example 8.

EXAMPLE 14

Aqueous N-sodium hydroxide solution (0.15 ml.) and benzoyl chloride (0.023 ml.) were successively added at 0° C. to a stirred solution of N-n-butyl-N-methyl-11-(3,17β-dihydroxyoestra-1,3,5(10)-trien-7α-yl)undecanamide (Example 2; 0.06 g.) in acetone (1 ml.) and the mixture was stirred at 0° C. for 30 minutes and poured into saturated aqueous sodium bicarbonate solution (10 ml.). The mixture was extracted three times with diethyl ether (15 ml. each time) and the combined extracts were washed with water (3 ml.), dried and evaporated to dryness. The residue was purified by chromatography on a silica gel column using a 3:2 v/v mixture of toluene and ethyl acetate as eluant. There was thus obtained as an oil N-n-butyl-N-methyl-11-(3-benzoyloxy-17β-hydroxyoestra-1,3,5(10)-trien-7α-yl)undecanamide, the structure of which was confirmed by proton magnetic resonance and mass spectroscopy.

EXAMPLE 15

Sodium hydride (0.005 g. of a 50% dispersion in mineral oil) was added to a stirred solution of N-n-butyl-11-(3,17β-dihydroxyoestra-1,3,5(10)-trien-7α-yl)-N-ethylundecanamide (Example 2; 0.052 g.) in tetrahydrofuran (2 ml.) and the mixture was stirred at laboratory temperature for 3.5 hours. Butyryl chloride (0.014 ml.) was added and the mixture was stirred at laboratory temperature for 16 hours, diluted with ethyl acetate (30 ml.) and filtered. The filtrate was washed with water, dried and evaporated to dryness. The residue was purified by chromatography on a silica gel column using a 1:1 v/v mixture of ethyl acetate and toluene as eluant. There was thus obtained as an oil N-n-butyl-11-(3-butyryloxy-17β-hydroxyoestra-1,3,5(10)-trien-7α-yl)-N-methylundecanamide, the structure of which was confirmed by proton magnetic resonance and mass spectroscopy.

The process described above was repeated using the appropriate acid chloride or acyl anhydride in place of butyryl chloride, and there were thus obtained the corresponding:

3-acetyl
3-propionyl
3-pivalyl
3-decanoyl
3-isopropoxycarbonyl
esters of N-n-butyl-11-(3,17β-dihydroxyoestra-1,3,5(10)-trien-7α-yl)-N-methylundecanamide.

EXAMPLE 16

Acetic anhydride (0.2 ml.) was added to a stirred solution of N-n-butyl-11-(3,17β-dihydroxyoestra-1,3,5(10)-trien-7α-yl)-N-methylundecanamide (Example 2; 0.052 g.) in pyridine (0.5 ml.) and the mixture was stirred at laboratory temperature for 16 hours. Water (0.1 ml.) was added and then toluene was added and distilled off until the mixture was free of acetic acid. The residue was purified by chromatography on a silica gel column using a 4:1 v/v mixture of toluene and ethyl acetate as eluant, and there was thus obtained as an oil N-n-butyl-11-(3,17β-diacetoxyoestra-1,3,5(10)-trien-7α-yl)-N-methylundecanamide, the structure of which was confirmed by proton magnetic resonance and mass spectroscopy.

The process described above was repeated using succinic anhydride in place of acetic anhydride, and there were thus obtained as oils N-n-butyl-11-[3,17β-di-(β-carboxypropionyl)oestra-1,3,5(10)-trien-7α-yl]-N-methylundecanamide and N-n-butyl-11-[17β-(β-carboxypropionyl)-3-hydroxyoestra-1,3,5(10)-trien-7α-yl]-N-methylundecanamide, which were separated one from the other during the chromatographic purification procedure, and the structures of which were confirmed as above.

EXAMPLE 17

Jones' Reagent (8N-chromic acid solution; 0.15 ml.) was added to a stirred solution of N-n-butyl-N-methyl-11-(3,17β-dihydroxyoestra-1,3,5(10)-trien-7α-yl)-undecanamide (Example 2; 0.262 g.) in acetone (15 ml.) at 0° C., and after 15 minutes isopropanol (0.1 ml.) was added and the mixture was evaporated to dryness. Water (15 ml.) was added and the mixture was adjusted to pH 8 with aqueous sodium bicarbonate solution and then extracted three times with methylene chloride (30 ml. each time). The combined extracts were washed with water (15 ml.), dried and evaporated to dryness, and the residue was purified by chromatography on a silica gel column using a 7:3 v/v mixture of toluene and ethyl acetate as eluant. There was thus obtained N-n-butyl-N-methyl-11-(3-hydroxy-17-oxooestra-1,3,5(10)-trien-7α-yl)undecanamide as an oil, the structure of which was confirmed by proton magnetic resonance and mass spectroscopy.

EXAMPLE 18

Lithium acetylide-ethylenediamine complex (0.097 g.) was added to a solution of N-n-butyl-N-methyl-11-(3-hydroxy-17-oxooestra-1,3,5(10)-trien-7α-yl)undecananamide (Example 17; 0.138 g.) in dimethyl sulphoxide and the mixture was kept at laboratory temperature for 4 hours. Water (0.1 ml.) was added, the mixture was evaporated to dryness and the residue was purified by chromatography on a silica gel column using a 7:3 v/v mixture of toluene and ethyl acetate as eluant. There was thus obtained N-n-butyl-N-methyl-11-(17α-ethynyl-3,17β-dihydroxyoestra-1,3,5(10)-trien-7α-yl)undecanamide as an oil, the structure of which was confirmed by proton magnetic resonance and mass spectroscopy.

EXAMPLE 19

The process described in Example 1 was repeated except that 11-(17α-ethynyl-3,17β-dihydroxyoestra-1,3,5(10)-trien-7α-yl)undecanoic acid and N-methyl-1H,1H-heptafluorobutylamine were used as starting materials. There was thus obtained 11-(17α-ethynyl-3,17β-dihydroxyoestra-1,3,5(10)-trien-7α-yl)-N-(1H,1H-heptafluorobutyl)-N-methylundecanamide as an oil, the structure of which was confirmed by proton magnetic resonance and mass spectroscopy.

The undecanoic acid used as starting material was obtained as follows:

The process described in Example 17 was repeated except that the corresponding undecanoic acid was used in place of the undecanamide, and that a 1:1 v/v mixture of toluene and ethyl acetate was used as eluant in the chromatographic purification. To a solution of the 11-(3-hydroxy-17-oxooestra-1,3,5(10-trien-7α-yl)undecanoic acid thus obtained (0.075 g.) in dimethyl sulphoxide (1 ml.) was added a 2-molar solution of dimsyl sodium in dimethyl sulphoxide (2 ml.) which had been saturated with acetylene gas, and the mixture was kept at laboratory temperature fo 18 hours, diluted with water (15 ml.,) acidified to pH 1 with aqueous N-hydrochloric acid, and extracted three times with ethyl acetate (10 ml. each time). The combined extracts were washed with water, dried and evaporated to dryness and the residue was purified by chromatography on a silica gel column using a 1:1 v/v mixture of toluene and ethyl acetate as eluant. There was thus obtained the desired 11-(17α-ethynyl-3,17β-dihydroxyoestra-1,3,5(10)trien-7α-yl)undecanoic acid.

EXAMPLE 20

A stirred mixture of cupric acetate (0.027 g.), iodine (0.038 g.), N-n-butyl-N-methyl-11-(3,17β-dihydroxyoestra-1,3,5(10)-trien-7α-yl)undecanamide (Example 2; 0.052 g.) and acetic acid (2 ml.) was heated at 55° C. for 18 hours and then poured into a mixture of ice (10 ml.) and saturated aqueous sodium bicarbonate solution (5 ml.). The mixture was extracted three times with ethyl acetate (15 ml. each time) and the combined extracts were washed with water, dried and evaporated to dryness. The residue was purified by chromatography on a silica gel column using a 3:2 v/v mixture of toluene and ethyl acetate as eluants and there were thus separately obtained N-n-butyl-N-methyl-11-(3,17β-dihydroxy-2-iodooestra-1,3,5(10)-trien-7α-yl)undecanamide (eluted first) and N-n-butyl-N-methyl-11-(3,17β-dihydroxy-4-iodooestra-1,3,5(10)-trien-7α-yl)undecanamide (eluted second).

EXAMPLE 21

The process described in the first two paragraphs of Example 1 was repeated except that 11-(17β-acetoxy-3-hydroxyoestra-1,3,5(10),6-tetraen-7-yl)undecanoic acid and N-methyl-N-butylamine were used as starting materials. There was thus obtained as an oil N-n-butyl-N-methyl-11-(3,17β-dihydroxyoestra-1,3,5(10),6-tetraen-7-yl)undecanamide, the structure of which was confirmed by proton magnetic resonance and mass spectroscopy.

The oestra-tetraene used as starting material was obtained as follows:

A solution of bromine (0.114 ml.) in acetic acid (2 ml.) was added dropwise to a stirred solution of 11-(17β-acetoxy-3-oxo-oestra-4-en-7α-yl)undecanoic acid (Example 2; 0.5 g.) in a mixture of diethyl ether (5 ml.) and acetic acid (2 ml.) which was cooled to 15° C. and the mixture was stirred at that temperature for 30 minutes and then poured into water (50 ml.). The mixture was extracted three times with methylene chloride (30 ml. each time) and the combined extracts were washed with water, dried and rapidly evaporated to dryness under reduced pressure at a bath temperature below 20° C. A solution of the residue, which consisted of 11-(17β-acetoxy-2,6-dibromo-3-oxooestr-4-en-7α-yl)undecanoic acid in dimethylformamide (3 ml.) was immediately added to a stirred mixture of lithium bromide (1.0 g.), lithium carbonate (1.0 g.) and dimethylformamide (10 ml.) which was heated under reflux, and the mixture was stirred and heated under reflux for 30 minutes and then evaporated to dryness under reduced pressure. Water (20 ml.) was added to the residue and the mixture was acidified to pH 1 with aqueous N-hydrochloric acid and extracted three times with methylene chloride (20 ml. each time). The combined extracts were washed with water, dried and evaporated to dryness and the residue was purified by chromatography on a silica gel column using a 7:3 v/v mixture of toluene and ethyl acetate as eluant. There was thus obtained as an oil 11-(17$\beta$-acetoxy-3-hydroxyoestra-1,3,5(10),6-tetraen-7-yl)undecanoic acid.

EXAMPLE 22

Butyl-lithium (0.8 ml. of a 1.6 molar solution in hexane) was added dropwise to a stirred solution of [9-(N-n-butyl-N-methylcarbamoyl)nonyl]triphenylphosphonium bromide (1.2 g.) in a mixture of dimethyl sulphoxide (2 ml.) and tetrahydrofuran (18 ml.), a solution of 3-benzyloxy-17$\beta$-hydroxyoestra-1,3,5(10),6,8(9),14(15)-hexaene-7-carboxaldehyde (0.05 g.) in tetrahydrofuran (2 ml.) was then added and the mixture was stirred at laboratory temperature for 1 hour and then evaporated to dryness under reduced pressure. Water (15 ml.) was added and the mixture was extracted three times with ethyl acetate (10 ml. each time) and the combined extracts were washed with water, dried and evaporated to dryness. The residue was purified by chromatography on a silica gel column using a 3:1 v/v mixture of petroleum ether (b.p. 60°–80° C.) and acetone as eluant. There was thus obtained as an oil 11-(3-benzyloxy-17$\beta$-hydroxyoestra-1,3,5(10),6,8(9),14(15)-hexaen-7-yl)-N-n-butyl-N-methylundec-10-enamide.

The above compound was hydrogenated by a similar process to that described in Example 4 and there was thus obtained as an oil N-n-butyl-N-methyl-11-(3,17$\beta$-dihydroxyoestra-1,3,5(10),6,8(9)-pentaen-7-yl)undecanamide, the structure of which was confirmed by proton magnetic resonance and mass spectroscopy.

The phosphonium bromide used as starting material was obtained as follows:

Triethylamine (6.5 ml.) and N-methyl-N-n-butylamine (5.5. ml.) were successively added to a stirred solution of 10-bromodecanoyl chloride (13 g.) in diethyl ether (100 ml.) which was maintained at 0° C. and the mixture was stirred at that temperature for 2 hours. Water (20 ml.) was added and the ethereal layer was separated, dried and evaporated to dryness. Triphenylphosphine (10.95 g.) was added to a stirred solution of the 10-bromo-N-n-butyl-N-methyldecanamide thus obtained (12.2 g.) in acetonitrile (125 ml.) and the mixture was stirred and heated under reflux for 16 hours and then evaporated to dryness under reduced pressure. The residue was dissolved in methylene chloride (50 ml.), diethyl ether (200 ml.) was added and the solvent was decanted off. There was thus obtained as solid residue [9-(N-n-butyl-N-methylcarbamoyl)nonyl]-triphenylphosphonium bromide which was used without further purification.

The steroidal carboxaldehyde used as starting material was obtained as follows:

17$\beta$-Acetoxy-6-bromo-7$\alpha$-cyanooestra-1,3,5(10)-trien-3-ol (Example 6, paragraph 4) was converted to the 3-benzyloxy derivative thereof by a similar process to that described in paragraph 5 of Example 6, and this compound was purified by chromatography on a silica gel column using a 19:1 v/v mixture of toluene and ethyl acetate as eluant.

2,3-Dichloro-5,6-dicyano-1,4-benzoquinone (1.03 g.) was added to a stirred solution of the above 3-benzyloxy compound (0.51 g.) in toluene (25 ml.) and the mixture was stirred and heated under reflux for 1 hour, cooled, diluted with diethyl ether (40 ml.) and washed three times with saturated aqueous sodium bicarbonate solution and once with water (50 ml. each time). The organic layer was dried and evaporated to dryness and the residue was purified by chromatography on a silica gel column using a 19:1 v/v mixture of toluene and ethyl acetate as eluant. There was thus obtained 17$\beta$-acetoxy-3-benzyloxyoestra-1,3,5(10),6,8(9),14(15)-hexaene-7-carbonitrile, which was reduced to the corresponding 7-carboxaldehyde by a similar process to that described in paragraph 6 of Example 6.

EXAMPLE 23

2,4-Bis-(p-methoxyphenyl)-1,3-dithia-2,4-diphosphetane-2,4-disulphide (Lawesson's Reagent; 0.375 g.) was added to a stirred solution of N-n-butyl-11-(3-methoxy-17$\beta$-tetrahydropyranyloxyoestra-1,3,5(10)-trien-7$\alpha$-yl)undecanamide (0.25 g.) in xylene (14 ml.) and the mixture was stirred and heated at 130° C. for 5 hours and then evaporated to dryness under reduced pressure. The residue was dissolved in a mixture of tetrahydrofuran (2 ml.), water (2 ml.) and acetic acid (4 ml.) and the solution was stirred at laboratory temperature for 16 hours and then evaporated to dryness under reduced pressure. The residue was purified by chromatography on a silica gel column using a 4:1 v/v mixture of toluene and ethyl acetate as eluant, and there was thus obtained as an oil N-n-butyl-11-(17$\beta$-hydroxy-3-methoxyoestra-1,3,5(10)-trien-7$\alpha$-yl)thioundecanamide.

Boron tribromide (0.5 ml.) was added to a stirred solution of the above thioamide (0.061 g.) in methylene chloride (3 ml.) which was cooled to $-20°$ C., and the mixture was stirred at that temperature for 4 hours and then poured into saturated aqueous sodium bicarbonate solution (2 ml.). The mixture was extracted three times with methylene chloride (2 ml. each time) and the combined extracts were washed with water, dried and evaporated to dryness. The residue was purified by chromatography as described above and there was thus obtained as an oil N-n-butyl-11-(3,17$\beta$-dihydroxyoestra-1,3,5(10)-trien-7$\alpha$-yl)thioundecanamide, the structure of which was confirmed by proton magnetic resonance and mass spectroscopy.

The tetrahydropyranyloxy-undecanamide used as starting material was obtained as follows:

The procedure described in the third, fourth, fifth and sixth paragraphs of Example 6 was repeated except that methyl iodide was used in place of benzylbromide in the fifth paragraph. There was thus obtained 17$\beta$-hydroxy-3-methoxyoestra-1,3,5(10)-trien-7$\alpha$-carboxaldehyde. Dihydropyran (2.4 ml.) and p-toluenesulphonic acid (4.46 ml. of an 0.1 molar solution in tetrahydrofuran) were successively added to a stirred solution of this aldehyde (2.8 g.) in methylene chloride (50 ml.) which was kept at 0° C., and after 5 minutes pyridine (0.2 ml.) was added and the mixture was washed with saturated aqueous sodium bicarbonate solution (5 ml.), dried and evaporated to dryness. The residue was purified by chromatography on a silica gel column using a 9:1 v/v mixture of toluene and ethyl acetate as eluant.

The 3-methoxy-17$\beta$-tetrahydropyranyloxyoestra-1,3,5(10)-trien-7$\alpha$-carboxaldehyde thus obtained was then converted to the desired amide by a similar procedure to that described in the last paragraph of Example 6 [reaction with (9-carboxynonyl)triphenylphosphonium bromide] followed by that described in the first paragraph of Example 6, except that n-butylamine was used in place of N-methylisobutylamine.

EXAMPLE 24

Triethylamine (0.053 g.) and methanesulphonyl chloride (0.044 g.) were successively added to a stirred solution of 17β-acetoxy-3-benzoyloxy-7α-(11-hydroxyundecyl)oestra-1,3,5(10)-triene (penultimate paragraph of Example 1; 0.206 g.) in methylene chloride (3 ml.) at −10° C., and the mixture was stirred for 30 minutes and then shaken with diethyl ether (30 ml.) and saturated aqueous sodium bicarbonate solution. The layers were separated, the aqueous layer was extracted with diethyl ether (30 ml.) and the combined ethereal solutions were washed with water (5 ml.), dried and evaporated to dryness. A mixture of the 11-methanesulphonyloxyundecyl compound thus obtained (0.228 g.) and diethylamine (4 ml.) was heated under reflux for 16 hours and evaporated to dryness. The residue was purified by chromatography on a silica gel column (Kieselgel 60) using a 4% v/v solution of triethylamine in toluene as eluant. There was thus obtained as an oil 17β-acetoxy-3-benzoyloxy-7α-(11-diethylaminoundecyl)oestra-1,3,5(10)-triene, the structure of which was confirmed by proton magnetic resonance and mass spectroscopy.

The above compound was hydrolysed by a similar process to that described in the second part of Example 1. There was thus obtained as an oil 7α-(11-diethylaminoundecyl)oestra-1,3,5(10)-triene-3,17β-diol, the structure of which was confirmed by proton magnetic resonance and mass spectroscopy.

EXAMPLE 25

− A mixture of 17β-acetoxy-3-benzoyloxy-7α-(11-methanesulphonyloxyundecyl)oestra-1,3,5(10)-triene (Example 24; 0.1 g.) and saturated methanolic ammonia solution (10 ml.) was heated in a sealed tube at 100° C. for 16 hours and was then evaporated to dryness. Butyryl chloride (0.2 ml.) was added to a stirred solution of the residue in pyridine (1 ml.) and the mixture was stirred at laboratory temperature for 16 hours, and then poured into water (10 ml.). The mixture was extracted three times with diethyl ether (10 ml. each time) and the combined extracts were washed with water (2 ml.), dried and evaporated to dryness. Aqueous N-sodium hydroxide solution (1 ml.) was added to a solution of the residue in methanol (5 ml.) and the mixture was kept at laboratory temperature for 18 hours, neutralised with aqueous N-hydrochloric acid and extracted three times with ethyl acetate (10 ml. each time). The combined extracts were washed with water (5 ml.), dried and evaporated to dryness and the residue was purified by chromatography on a silica gel column using a 1:1 v.v mixture of toluene and ethyl acetate as eluant. There was thus obtained as an oil N-[N-(3,17β-dihydroxyoestra-1,3,5(10)-trien-7α-yl)undecyl]butyramide, the structure of which was confirmed by proton magnetic resonance and mass spectroscopy.

EXAMPLE 26

The process described in the last paragraph of Example 6 was repeated except that (8-hexanamidooctyl)triphenylphosphonium bromide was used in place of (9-carboxynonyl)triphenylphosphonium bromide. The hydrogenation process described in the second paragraph of Example 6 was then repeated using the N-[9-(3-benzyloxy-17β-hydroxyoestra-1,3,5(10)-trien-7α-yl)non-8-enyl]hexanamide thus obtained as starting material, and there was thus obtained as an oil N-[9-(3,17β-dihydroxyoestra-1,3,5(10)-trien-7α-yl)nonyl]hexanamide, the structure of which was confirmed by proton magnetic resonance and mass spectroscopy.

The (8-hexanamidooctyl)triphenylphosphonium bromide used as starting material was obtained as follows:

Triethylamine (0.35 ml.) and hexanoyl chloride (0.35 ml.) were successively added to a stirred solution of 8-bromooctylamine (0.5 g.) in diethyl ether (5 ml.) and the mixture was stirred at laboratory temperature for 1 hour. Saturated aqueous sodium bicarbonate solution (5 ml.) was added, the ethereal layer was separated and the aqueous layer was extracted three times with diethyl ether (5 ml. each time). The combined ethereal solutions were washed with water (2 ml.), dried and evaporated to dryness. Triphenylphosphine (0.331 g.) was added to a stirred solution of the above N-(8-bromoethyl)hexanamide (0.385 g.) in acetonitrile (10 ml.) and the mixture was stirred and heated under reflux for 16 hours and then evaporated to dryness. The residue was stirred with diethyl ether and the ethereal solution was decanted off. There was thus obtained as residual gum (8-hexanamidooctyl)triphenylphosphonium bromide which was used without further purification.

EXAMPLE 27

The procedure described in the last paragraph of Example 6 was repeated except that (7-N-methylcarbamoylheptyl)triphenylphosphonium bromide (prepared from 8-bromo-N-methyloctanamide and triphenylphosphine by a similar process to that described in the last part of Example 22) was used in place of (9-carboxynonyl)triphenylphosphonium bromide. The hydrogenation process described in the second paragraph of Example 6 was then repeated using the 9-(3-benzyloxy-17β-hydroxyoestra-1,3,5(10)trien-7α-yl)-N-methylnon-8-enamide thus obtained as starting material, and there was thus obtained as an oil 9-(3,17β-dihydroxyoestra-1,3,5(10)-trien-7α-yl)-N-methyl-nonanamide, the structure of which was confirmed by proton magnetic resonance and mass spectroscopy.

EXAMPLE 28

A mixture of 9-(3,17β-dihydroxyoestra-1,3,5(10)-trien-7α-yl)-N-methylnonanamide (Example 27; 0.047 g.) and a molar solution of borane in tetrahydrofuran (5 ml.) was heated under reflux for 2 hours, cooled and concentrated aqueous hydrochloric acid (2 ml.) was added. The tetrahydrofuran was removed by evaporation and the residue was basified with aqueous 5N-sodium hydroxide solution and extracted three times with ethyl acetate (10 ml. each time). The combined extracts were washed with water (2 ml.), dried and evaporated to dryness. There was thus obtained as an oil 7α-(9-methylaminononyl)oestra-1,3,5(10)-triene-3,17β-diol, the structure of which was confirmed by proton magnetic resonance and mass spectroscopy.

EXAMPLE 29

Hexanoyl chloride (0.5 ml.) was added to a solution of 7α-(9-methylaminononyl)oestra-1,3,5(10)-trien-3,17β-diol (Example 28; 0.037 g.) in pyridine (5 ml.) and the mixture was kept at laboratory temperature for 16 hours and then extracted with ethyl acetate (20 ml.). The extract was washed successively with aqueous 2N-hydrochloric acid (5 ml.), saturated aqueous sodium bicarbonate solution (5 ml.) and water (2 ml.), dried and evaporated to dryness. The residue was purified by chromatography on a silica gel column using a 9:1 v/v mixture of toluene and ethyl acetate as eluant, and there was thus obtained N-[9-(3,17β-dihexanoyloxyoestra-1,3,5(10)-trien-7α-yl)nonyl]-N-methylhexanamide. A solution of this compound (0.027 g.) in methanol (5 ml.) and aqueous 2N-sodium hydroxide solution (2 m.) were stirred at laboratory temperature for 16 hours and the mixture was then extracted three times with ethyl acetate (10 ml. each time). The combined extracts were washed with water, dried and evaporated to dryness and there was thus obtained as residual oil N-[9-(3,17β-dihydroxyoestra-1,3,5(10)-trien-7α-yl)nonyl]-N-methylhexanamide, the structure of which was confirmed by proton magnetic resonance and mass spectroscopy.

EXAMPLE 30

N-Methylmorpholine (0.028 ml.) and isobutyl chloroformate (0.038 ml.) were successively added to a stirred solution of 7α-(9-methylaminononyl)oestra-1,3,5(10)-trien-3,17β-diol (Example 28; 0.08 g.) in tetrahydrofuran (3 ml.) and the mixture was stirred at laboratory temperature for 150 minutes. Saturated aqueous sodium bicarbonate solution (2 ml.) was added and the mixture was extracted three times with methylene chloride (10 ml. each time). The combined extracts were washed with water (5 ml.), dried and evaporated to dryness and there was thus obtained as residual oil isobutyl N-[9-(3,17β-dihydroxyoestra-1,3,5(10)-trien-7α-yl)nonyl]-N-methylcarbamoate.

EXAMPLE 31

The process described in Example 25 was repeated except that 17β-acetoxy-3-methoxy-7α-(9-methanesulphonyloxynonyl)oestra-1,3,5(10)-triene was reacted with ammonia, and that the resulting 9-aminononyl compound was reacted with n-butyl isocyanate. The 17β-acetoxy group was removed by hydrolysis with aqueous methanolic sodium hydroxide solution, and the 3-methoxy group was converted to a hydroxy group with boron tribromide by a similar process to that described in the second paragraph of Example 8. There was thus obtained N¹-n-butyl-N³-[9-(3,17β-dihydroxyoestra-1,3,5(10)-trien-7α-yl)nonyl]urea, the structure of which was confirmed by proton magnetic resonance and mass spectroscopy.

The steroidal starting material was prepared by a similar process to that described in Examples 1 and 24, except that 9-bromononanol was used in place of 11-bromoundecanol in the third paragraph of Example 1, and that the benzoylation step described in the eighth paragraph of Example 1 was replaced by the methylation step described in the fourth paragraph of Example 8.

EXAMPLE 32

A solution of sodium thiobutoxide [generated from butanethiol (0.045 g.) and a 60% dispersion of sodium hydride in mineral oil (0.02 g.)] in tetrahydrofuran (2 ml.) was added to a solution of 17β-acetoxy-3-benzoyloxy-7α-(11-methanesulphonyloxyundecyl)oestra-1,3,5(10)-triene (Example 24; 0.078 g.) in tetrahydrofuran (1 ml.) and the mixture was kept for 1 hour at laboratory temperature, neutralised with aqueous N-hydrochloric acid and extracted three times with ethyl acetate (10 ml. each time). The combined extracts were washed with water (3 ml.), dried and evaporated to dryness, and the residue was dissolved in methanol (3 ml.). Aqueous N-sodium hydroxide solution (1 ml.) was added and the mixture was kept at laboratory temperature for 18 hours, neutralised with aqueous N-hydrochloric acid and extracted three times with ethyl acetate (10 ml. each time). The combined extracts were washed with water (10 ml.), dried and evaporated to dryness and the residue was purified by chromatography on a silica gel column using a 4:1 v/v mixture of toluene and ethyl acetate as eluant. There was thus obtained as an oil 7α-(11-n-butylthioundecyl)oestra-1,3,5(10)-triene-3,17β-diol, the structure of which was confirmed by proton magnetic resonance and mass spectroscopy.

EXAMPLE 33

A solution of sodium metaperiodate (0.016 g.) in water (0.5 ml.) was added to a solution of 7α-11-n-butylthioundecyl)oestra-1,3,5(10)-triene-3,17β-diol (Example 32; 0.035 g.) in methanol (1 ml.) and the mixture was stirred at laboratory temperature for 18 hours, evaporated to dryness and evaporated from toluene to remove the last traces of water. The residue was extracted three times with acetone and the combined extracts were evaporated to dryness. There was thus obtained as an oil 7α-(11-n-butylsulphinylundecyl)oestra-1,3,5(10)-triene-3,17β-diol, the structure of which was confirmed by proton magnetic resonance and mass spectroscopy.

EXAMPLE 34 m-Chloroperbenzoic acid (0.026 g.) was added to a solution of 7α-(11-n-butylthioundecyl)oestra-1,3,5(10)-triene-3,17β-diol (Example 32; 0.035 g.) in chloroform (1 ml.) and the mixture was kept for 2 hours at laboratory temperature and then evaporated to dryness. The residue was shaken with water (2 ml.) and the mixture extracted three times with ethyl acetate (10 ml. each time). The combined extracts were washed with saturated aqueous sodium bicarbonate solution and then with water, dried and evaporated to dryness. There was thus obtained as residual oil 7α-(11-n-butylsulphonylundecyl)oestra-1,3,5(10)-triene-3,17β-diol, the structure of which was confirmed by proton magnetic resonance and mass spectroscopy.

EXAMPLE 35

The process described in Examples 32, 33 and 34 was repeated using the appropriate thiol and the appropriate 7α-(ω-methanesulphonyloxyalkyl)-steroidal derivative as initial starting materials in the process of Example 32. There were thus obtained as oils the compounds described in the following table:

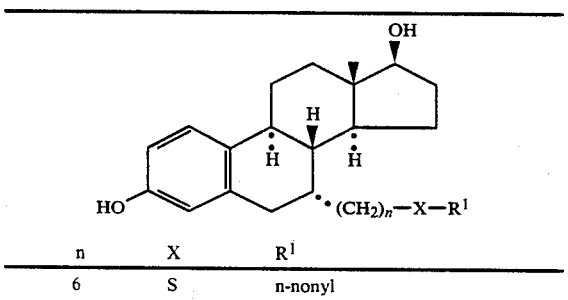

| n | X | R¹ |
|---|---|---|
| 6 | S | n-nonyl |

-continued

[Structure: steroidal estradiol-like skeleton with OH at 17, HO at 3, and 7α-(CH₂)ₙ—X—R¹ substituent]

| n | X | R¹ |
|---|---|---|
| 9 | S | n-hexyl |
| 9 | S | n-heptyl |
| 9 | S | 4,4,5,5,5-pentafluoropentyl |
| 9 | S | p-chlorophenyl |
| 9 | S | p-chlorobenzyl |
| 9 | S | p-chlorophenethyl |
| 10 | S | n-pentyl |
| 10 | S | 4,4,4-trifluorobutyl |
| 10 | S | 4,4,5,5,5-pentafluoropentyl |
| 10 | S | 1H,1H—heptafluorobutyl |
| 10 | S | m-chlorophenyl |
| 10 | S | p-chlorophenyl |
| 10 | S | p-fluorophenyl |
| 10 | S | p-bromophenyl |
| 10 | S | p-chlorobenzyl |
| 10 | S | p-chlorophenethyl |
| 11 | S | 4,4,4-trifluorobutyl |
| 6 | SO | n-nonyl |
| 9 | SO | n-hexyl |
| 9 | SO | n-heptyl |
| 9 | SO | 4,4,5,5,5-pentafluoropentyl |
| 9 | SO | p-chlorophenyl |
| 9 | SO | p-chlorobenzyl |
| 9 | SO | p-chlorophenethyl |
| 10 | SO | n-pentyl |
| 10 | SO | 4,4,4-trifluorobutyl |
| 10 | SO | 4,4,5,5,5-pentafluoropentyl |
| 10 | SO | 1H,1H—heptafluorobutyl |
| 10 | SO | p-chlorophenyl |
| 10 | SO | p-fluorophenyl |
| 10 | SO | p-bromophenyl |
| 10 | SO | p-chlorobenzyl |
| 10 | SO | p-chlorophenethyl |
| 11 | SO | 4,4,4-trifluorobutyl |
| 9 | SO₂ | n-heptyl |
| 10 | SO₂ | p-chlorobenzyl |
| 10 | SO₂ | p-chlorophenethyl |

The 7α-(ω-methanesulphonyloxyalkyl)-steroidal derivatives used as starting materials were obtained as described in Example 24 from the corresponding 7α-(ω-hydroxyalkyl)-steroidal derivatives which in turn were obtained as described in Example 1 using the appropriate ω-(dimethyl-t-butylsilyloxy)alkyl bromide in place of 11-(dimethyl-t-butylsilyloxy)undecyl bromide as intermediate.

EXAMPLE 36

The process described in the penultimate paragraph of Example 3 was repeated except that [4-(N-heptylsulphamoyl)butyl]triphenylphosphonium bromide was used in place of (4-carboxybutyl)triphenylphosphonium bromide. There was thus obtained as an oil N-heptyl-7-(3,17β-dihydroxyoestra-1,3,5(10)-trien-7α-yl)hept-4-enesulphonamide, the structure of which was confirmed by proton magnetic resonance and mass spectroscopy. Both the 3-benzoyl and 17-acetyl groups were removed during the reaction, by contrast with Example 3 wherein only the 3-benzoyl group was removed.

The phosphonium bromide used as starting material was obtained as follows:

Sodium iodide (1.1 g.) was added to a solution of 1,4-butanesultone (1.0 g.) in acetone (10 ml.) and the mixture was heated under reflux for 1 hour, cooled and filtered. Dimethylformamide (0.05 ml.) and oxalyl chloride (0.475 ml.) were successively added to a stirred solution of the sodium 4-iodobutanesulphonate thus obtained (1.32 g.) in toluene (20 ml.) and the mixture was stirred at laboratory temperature for 3 hours, filtered and the filtrate was evaporated to dryness.

Triethylamine (0.65 ml.) and n-heptylamine (0.68 ml.) were successively added to a solution of the 4-iodobutanesulphonyl chloride thus obtained (1.3 g.) in diethyl ether (30 ml.) and the mixture was kept at laboratory temperature for 2 hours and then evaporated to dryness. The residue was dissolved in ethyl acetate and the solution was washed twice with water (5 ml. each time), dried and evaporated to dryness. The residue was purified by chromatography on a silica gel column using methylene chloride as eluant, and there was thus obtained N-heptyl-4-iodobutanesulphonamide.

A mixture of the above sulphonamide (0.25 g.), triphenylphosphine (0.18 g.) and toluene (10 ml.) was heated under reflux for 2 hours and then cooled, and the toluene solution was decanted off the oil which formed. The oil was washed with more toluene, and then used without further purification. It consisted of 4-(N-heptylsulphamoyl)butyl]triphenylphosphonium bromide.

EXAMPLE 37

A solution of N-heptyl-7-(3,17β-dihydroxy-oestra-1,3,5(10)-trien-7α-yl)hept-4-enesulphonamide (Example 36; 0.04 g.) in ethyl acetate (10 ml.) was stirred with a 10% palladium-on-charcoal catalyst (0.01 g.) at laboratory temperature for 90 minutes and then filtered, and the filtrate was evaporated to dryness. There was thus obtained as residual oil N-heptyl-7-(3,17β-dihydroxyoestra-1,3,5(10)-trien-7α-yl)heptanesulphonamide, the structure of which was confirmed by proton magnetic resonance and mass spectroscopy.

EXAMPLE 38 n-Butyl-lithium (0.27 ml. of a 1.5 molar solution in diethyl ether) was added to a stirred solution of 11-(17β-acetoxy-3-hydroxyoestra-1,3,5(10)-trien-7α-yl)undecanoic acid (Example 2; 0.046 g.) in tetrahydrofuran (1 ml.) and the mixture was stirred at laboratory temperature for 2 hours. Saturated aqueous sodium hydrogen tartrate solution (2 ml.) was added and the mixture was extracted three times with ethyl acetate (5 ml. each time). The combined extracts were washed with water, dried and evaporated to dryness and the residue was purified by chromatography on a silica gel column using a 17:3 v/v mixture of toluene and ethyl acetate as eluant. There was thus obtained as an oil 15-(3,17β-dihydroxyoestra-1,3,5(10)-trien-7α-yl)pentadecan-5-one, the structure of which was confirmed by proton magnetic resonance and mass spectroscopy.

EXAMPLE 39 n-Butyl-lithium (0.341 ml. of a 1.6 molar solution in hexane) was added to a stirred solution of 2-oxotridecylphosphonate (0.193 g.) in tetrahydrofuran (10 ml.) which was maintained at −70° C. and the mixture was stirred at that temperature for 40 minutes. A solution of 3-(17β-acetoxy-3-benzoyloxyoestra-1,3,5(10)-trien-7α-yl)propionaldehyde (Example 3; 0.2 g.) in tetrahydrofuran (10 ml.) was added and the mixture was allowed to warm up to laboratory temperature and was stirred at that temperature for 4.5 hours. Acetic acid was added until the mixture was acidic and the mixture was evaporated to dryness. Water (10 ml.) was added and the mixture was extracted three times with ethyl acetate (30 ml. each time). The combined extracts were washed with water, dried and evaporated to dryness and there was thus obtained as residual oil 1-(17β-acetoxy-3-benzoyloxyoestra-1,3,5(10)-trien-7α-yl)hexadec-3-en-5-one.

The above compound was hydrogenated by a similar process to that described in Example 4, and there was thus obtained as an oil 1-(17β-acetoxy-3-benzoyloxyoestra-1,3,5(10)-trien-7α-yl)hexadecan-5-one.

The above compound was hydrolysed by a similar process to that described in the second paragraph of Example 1, and there was thus obtained 1-(3,17β-dihydroxyoestra-1,3,5(10)-trien-7α-yl)hexadecan-5-one, which was purified by chromatography on a silica gel column using a 4:1 v/v mixture of toluene and ethyl acetate as eluant.

EXAMPLE 40

The process described in Example 26 was repeated using [3-(5-N-n-butyl-N-methylcarbamoyl pentyloxy)-propyl]triphenylphosphonium bromide and 3-benzyloxy-17β-hydroxyoestra-1,3,5(10)-triene-7α-carboxaldehyde (Example 6) as starting materials. There was thus obtained after simultaneous hydrogenolysis and hydrogenation, as an oil, 6-[4-(3,17β-dihydroxyoestra-1,3,5(10)-triene-7α-yl)butoxy]-N-n-butyl-N-methylhexanamide, the structure of which was confirmed by proton magnetic resonance and mass spectroscopy.

The triphenylphosphonium bromide used as starting material was obtained from 6-bromohexanoic acid by reaction with oxalyl chloride and N-methyl-n-butylamine to form the amide, then with 1,3-trimethylene glycol and sodium hydride in dimethylformamide to form the 6-(3-hydroxypropoxy)hexanamide, followed by conversion of the 3-hydroxy group to a 3-bromo group with bromine and triphenylphosphine in dimethylformamide and finally reaction with triphenylphosphine in toluene.

EXAMPLE 41

A mixture of 7α-(10-mesyloxydecyl)oestra-1,3,5(10)-triene-3,17β-diol (0.07 g.) and N-methylhexylamine (0.5 ml.) was heated at 75° C. for 2 hours and the excess of N-methylhexylamine was removed by evaporation. The residue was purified by chromatography on a silica gel column using a 24:1 v/v mixture of ethyl acetate and triethylamine as eluant, and there was thus obtained as an oil 7α-(10-N-methylhexylaminodecyl)oestra-1,3,5(10)-trien-3,17β-diol, the structure of which was confirmed by proton magnetic resonance and mass spectroscopy.

The process described above was repeated using N-methyl-4,4,5,5,6,6,6-heptafluorohexylamine or N-methyl-p-chlorophenethylamine in place of N-methylhexylamine, and there were thus obtained respectively 7α-[10-(N-methyl-4,4,5,5,6,6,6-heptafluorohexylamino)decyl]- and 7α-(10-N-methyl-p-chlorophenethylaminodecyl)-oestra-1,3,5(10)-trien-3,17β-diol.

The 7α-mesyloxydecyl-oestradiol used as starting material was obtained from 3-benzyloxy-17β-hydroxyoestra-1,3,5(10)-triene-7α-carboxaldehyde (described in Example 6) by reaction with 9-(dimethyl-t-butylsilyloxynonyl)triphenylphosphonium bromide (prepared from 9-bromononanol, dimethyl-t-butylsilyl chloride and triphenylphosphine) by a similar process to that described in the last paragraph of Example 6, followed by acid hydrolysis of the silyl group, mesylation of the decenol thus obtained and simultaneous hydrogenation of the mesyloxydecene side-chain to a mesyloxydecane side-chain and hydrogenolysis of the 3-benzyloxy group.

EXAMPLE 42 m-Chloroperbenzoic acid (0.02 g.) was added to a solution of 7α-(10-N-methylhexylaminodecyl)-oestra-1,3,5(10)-triene-3,17β-diol (Example 41; 0.047 g.) in methylene chloride (8 ml.) and the mixture was kept at laboratory temperature for 2.5 hours. Methylene chloride (20 ml.) was added and the solution was washed successively with saturated aqueous sodium sulphite solution, saturated aqueous sodium bicarbonate solution and water (5 ml. each time), dried and evaporated to dryness. The residue was purified by chromatography on a silica gel column using a 7:2:1 v/v/v mixture of ethyl acetate, methanol and triethylamine as eluant. There was thus obtained as an oil 7α-(10-N-methyl-N-hexylaminodecyl)oestra-1,3,5(10)-triene-3,17β-diol-N-oxide, the structure of which was confirmed by proton magnetic resonance and mass spectroscopy.

The N-oxides of 7α-[10-(N-methyl-4,4,5,5,6,6,6-heptafluorohexylamino)decyl]- and 7α-(10-N-methyl-p-chlorophenethylaminodecyl)oestra-1,3,5(10)-triene-3,17β-diol (also described in Example 41) were similarly obtained by oxidation with m-chlorobenzoic acid.

EXAMPLE 43

The process described in Example 32 was repeated using 7α-(7-mesyloxyheptyl)oestra-1,3,5(10)-triene-3,17β-diol (obtained as described in Example 41 using initially 6-(dimethyl-t-butylsilyloxy)hexyltriphenylphosphonium bromide) and 2-n-pentylthio-ethanol (obtained from pentanethiol and 2-bromoethanol) as starting materials. There was thus obtained as an oil 7α-[7-(2-n-pentylthioethoxy)heptyl]oestra-1,3,5(10)-triene-3,17β-diol, the structure of which was confirmed by proton magnetic resonance and mass spectroscopy.

The above compound was oxidised with sodium metaperiodate by a similar process to that described in Example 33, and there was thus obtained 7α-[7-(2-n-pentylsulphinylethoxy)heptyl]oestra-1,3,5(10)-triene-3,17β-diol.

EXAMPLE 44

The process described in Example 32 was repeated using 7α-(6-mesyloxyhexyl)oestra-1,3,5(10)-triene-3,17β-diol (obtained as described in Example 41 using initially 5-(dimethyl-t-butylsilyloxy)pentyltriphenylphosphonium bromide and 3-n-pentylthiopropanethiol (obtained from trimethylene-1,3-dithiol and pentyl bromide) as starting materials. There was thus obtained as an oil 7α-[6-(3-n-pentylthiopropylthio)hexyl]-oestra-1,3,5(10)triene-3,17β-diol, the structure of which was confirmed by proton magnetic resonance and mass spectroscopy.

The above compound was oxidised with sodium metaperiodate by a similar process to that described in Example 33, and there was thus obtained 7α-[6-(3-n-pentylsulphinylpropylsulphinyl)hexyl]oestra-1,3,5(10)-triene-3,17β-diol.

EXAMPLE 45

The process described in Example 1 was repeated using N-methyl-n-butylamine and 3-[7-(3,17β-dihydroxyoestra-1,3,5(10)-triene-7α-yl)heptylthio]propionic acid as starting materials. There was thus obtained as an oil 3-[7-(3,17β-dihydroxyoestra-1,3,5(10)-triene-7α-yl)heptylthio]-N-n-butyl-N-methylpropionamide, the structure of which was confirmed by proton magnetic resonance and mass spectroscopy.

The propionic acid used as starting material was obtained by the reaction of 7α-(7-mesyloxyheptyl)oestra-1,3,5(10)-triene-3,17β-diol (obtained as described in Example 41 using initially 6-(dimethyl-t-butylsilyloxy)-hexyltriphenylphosphonium bromide) with methyl 3-mercaptopropionate, followed by alkaline hydrolysis of the methyl ester.

EXAMPLE 46

A mixture of 7α-(10-mesyloxydecyl)oestra-1,3,5(10)-triene-3,17β-diol (Example 41; 0.1 g.), sodium iodide (0.034 g.), butylmethylphenylphosphine (0.039 ml.) and acetonitrile (5 ml.) was heated under reflux for 16 hours, evaporated to dryness and the residue was dissolved in methylene chloride (20 ml.). The mixture was filtered and the filtrate was diluted with diethyl ether (100 ml.). The mixture was filtered and the solid residue, which consisted of butyl[10-(3,17β-dihydroxyoestra-1,3,5(10)-triene-7α-yl)decyl]methylphenylphosphonium iodide, was dissolved in a mixture of tetrahydrofuran (6 ml.) and dimethyl sulphoxide (1 ml.). n-Butyl-lithium (0.5 ml. of a 1.6M molar solution in hexane) was added and the mixture was stirred at laboratory temperature for 90 minutes. Water (10 ml.) was added and the mixture was extracted three times with ethyl acetate (10 ml. each time). The combined extracts were washed with water, dried and evaporated to dryness and the residue was purified by chromatography on a silica gel column using a 97:3 v/v mixture of methylene chloride and methanol as eluant. There were thus obtained as oils a less polar substance 7α-(10-butylphenylphosphinyldecyl)oestra-1,3,5(10)-triene-3,17β-diol and a more polar substance 7α-(10-methylphenylphosphinyldecyl)oestra-1,3,5(10)-triene-3,17β-diol, the structures of both of which were confirmed by proton magnetic resonance and mass spectroscopy.

EXAMPLE 47

A mixture of butyl[10-(3,17β-dihydroxyoestra-1,3,5(10)-triene-7α-yl)decyl]methylphenylphosphonium iodide (Example 46; 0.05 g.), tetrahydrofuran (5 ml.) and aqueous 30% sodium hydroxide solution (2 ml.) was stirred at laboratory temperature for 18 hours, diluted with water (10 ml.) and extracted three times with ethyl acetate (10 ml. each time). The combined extracts were washed with water, dried and evaporated to dryness and the residue was purified by chromatography on a silica gel column using a 25:1 v/v mixture of methylene chloride and methanol as eluant. There was thus obtained as an oil 7α-(10-butylmethylphosphinyldecyl)oestra-1,3,5(10)-triene-3,17β-diol, the structure of which was confirmed by proton magnetic resonance and mass spectroscopy.

What we claim is:

1. A steroid derivative of the formula:

$$ST-A-X-R^1$$

wherein ST is a 7α-linked steroid nucleus of the general formula:

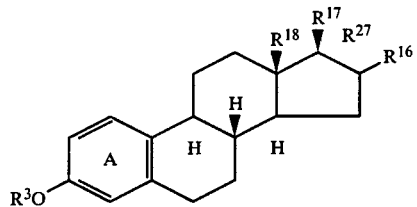

wherein the dotted lines between carbon atoms 6 and 7, and carbon atoms 8 and 9, of the steroid nucleus indicate that there is an optional double bond between carbon atoms 6 and 7, or that there are two optional double bonds between carbon atoms 6 and 7 and carbon atoms 8 and 9;

wherein the aromatic ring A may optionally bear one or two of a member selected from the group consisting of halogen and alkyl substituents;

wherein $R^3$ is hydrogen or alkyl, alkanoyl, alkoxycarbonyl, carboxyalkanoyl or aroyl each of up to 10 carbon atoms;

wherein $R^{16}$ is hydrogen, alkyl of up to 6 carbon atoms which is preferably in the β-configuration, or hydroxy which is preferably in the α-configuration;

wherein either $R^{17}$ (in the β-configuration) is hydroxy or alkanoyloxy, carboxyalkanoyloxy or aroyloxy each of up to 10 carbon atoms; and $R^{27}$ (in the α-configuration) is hydrogen or alkyl, alkenyl or alkynyl each of up to 6 carbon atoms; or $R^{17}$ and $R^{27}$ together form oxo (=O);

wherein $R^{18}$ is alkyl of up to 6 carbon atoms;

wherein A is straight-or branched-chain alkylene, alkenylene or alkynylene each of from 3 to 14 carbon atoms, which may have one or more hydrogen atoms replaced by fluorine atoms, or has the formula $$-A^1-Y-A^{11}-$$

wherein $A^1$ and $A^{11}$ are each alkylene or alkenylene, optionally fluorinated, having together a total of 2 to 13 carbon atoms and Y is —O—, —S—, —SO—, and —SO$_2$—, —CO— or —NR— wherein R is hydrogen or alkyl of up to 3 carbon atoms;

or $A^1$ is alkylene or alkenylene, optionally fluorinated, and $A^{11}$ is a direct link or alkylene or alkenylene, optionally fluorinated, such that $A^1$ and $A^{11}$ together have a total of 1 to 12 carbon atoms, and Y is —NRCO—, —CONR—, —COO—, —OCO— or phenylene wherein R has the meaning stated above;

wherein $R^1$ is hydrogen, or alkyl, alkenyl, cycloalkyl, halogenoalkyl, carboxyalkyl, alkoxycarbonylalkyl, aryl or arylalkyl each of up to 10 carbon atoms, or dialkylaminoalkyl wherein each alkyl is of up to 6 carbon atoms, or $R^1$ is joined to $R^2$ as defined below;

and wherein X is —CONR$^2$—, —CSNR$^2$—, —NR$^{12}$—CO—, $$-NR^{12}-\overset{NR^{22}}{\underset{\|}{C}}-NR^2-,$$

—NR$^{12}$—CS—, —NR$^{12}$—CONR$^2$—, —SO$_2$NR$^2$— or —CO—;

or, when $R^1$ is not hydrogen, is —O—, —$NR^2$—, —(NO)$R^2$—, —(PO)$R^2$—, —$NR^{12}$—COO—; —$NR^{12}$—$SO_2$—, —S—, —SO— or —$SO_2$—;

wherein $R^2$ is hydrogen or alkyl of up to 6 carbon atoms, or $R^1$ and $R^2$ together form alkylene or halogenoalkylene such that, with the adjacent nitrogen atom, they form a heterocyclic ring of 5 to 7 ring atoms, one of which atoms may be a second heterocyclic atom selected from oxygen, sulphur and nitrogen;

wherein $R^{12}$ is hydrogen or alkyl of up to 6 carbon atoms; and wherein $R^{22}$ is hydrogen, cyano or nitro; or a salt thereof when appropriate.

2. A steroid derivative as claimed in claim 1 which has the formula:

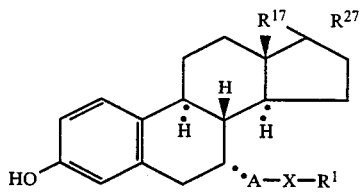

wherein $R^{17}$ is hydroxy and $R^{27}$ is hydrogen or ethynyl, or $R^{17}$ and $R^{27}$ together form oxo;

wherein —A— is —(CH$_2$)$_n$—, wherein n is an integer from 3 to 14, or —A— is:

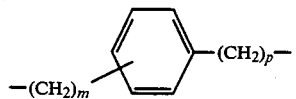

wherein m is an integer from 2 to 9 and p is 0 to 2;

wherein $R^1$ is alkyl, fluoroalkyl or cycloalkyl each of up to 10 carbon atoms, or phenyl, chlorophenyl or benzyl, or is linked to $R^2$ as stated below;

wherein X is —CONR$^2$—, —NR$^{12}$CO—, —S—, —SO— or —SO$_2$—, wherein $R^2$ is hydrogen or alkyl of up to 3 carbon atoms or together with $R^1$ forms alkylene of 5 or 6 carbon atoms, and wherein $R^{12}$ is hydrogen or alkyl of up to 3 carbon atoms.

3. A steroid derivative as claimed in claim 2 wherein the number of carbon atoms in the two groups A and $R^1$ adds up to between 12 and 16 inclusive.

4. A process for the manufacture of a steroid derivative claimed in claim 1, which comprises:

(a) when X has the formula —CONR$^2$—, —CSNR$^2$— or —SO$_2$NR$^2$—, the reaction of a compound of the formula ST$^1$—A—Z$^1$, wherein A has the meaning stated in claim 1, wherein ST$^1$ either has the same meaning as stated in claim 1 for ST, or is an equivalent 7α-linked steroid nucleus which bears one or more protecting groups for functional derivatives, and wherein Z$^1$ is an activated group derived from a carboxylic, thiocarboxylic or sulphonic acid, with an amine of the formula HNR$^1$R$^2$, wherein R$^1$ and R$^2$ have the meanings stated in claim 1;

or (b) when X has the formula —CO—, the reaction of an acid of the formula ST$^1$ —A—COOH, wherein ST$^1$ and A have the meanings stated above, with an organometallic compound of the formula R$^1$—M, wherein R$^1$ has the meaning stated above and M is a metal group;

or (c) when X has the formula —S—, —O—, —NR$^2$— or (PO)R$^2$ the reaction of a compound of the formula ST$^1$—A—Z$^2$, wherein ST$^1$ and A have the meanings stated above and wherein Z$^2$ is a displaceable group, with a compound of the formula R$^1$SH, R$^1$OH, HNR$^1$R$^2$ or R$^1$R$^2$P—C$_6$H$_5$, wherein R$^1$ and R$^2$ have the meanings stated above, whereafter a phosphonium salt is hydrolysed to the phosphinyl compound;

or (d) when X has the formula —NR$^{12}$CO—, —NR$^{12}$CS—, —NR$^{12}$CONR$^2$—,

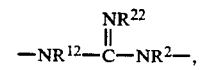

—NR$^{12}$COO— or —NR$^{12}$SO$_2$—, the reaction of a compound of the formula ST$^1$—A—NHR$^{12}$, wherein ST$^1$, A and R$^{12}$ have the meanings stated above, with an acylating agent derived from an acid of the formula R$^1$COOH, R$^1$CSOH, R$^1$OCOOH or R$^1$SO$_2$OH; or, for the manufacture of a urea, with an isocyanate of the formula R$^1$NCO; or, for the manufacture of a guanidine, with a cyanamide of the formula R$^1$NR$^2$—CN;

or (e) when —A— is alkenylene of the formula —A$^3$—CH=CH—A$^4$—, the reaction of a compound of the formula:

wherein ST$^1$ and A$^3$ have the meanings stated above, with a triphenylphosphonium salt of the formula:

wherein $R^1$, X and A$^4$ have the meanings stated above and wherein Q$^-$ is an anion; wherafter:

(i) any protecting group in ST$^1$ is removed by conventional means;

or (ii) a steroid derivative wherein ST is a 17-hydroxy-steroid derivative may be converted by conventional reactions into the corresponding 17-keto steroid derivative, and thence to the corresponding 17-hydroxy-17-hydrocarbyl steroid derivative (that is, a steroid derivative wherein R$^{27}$ is alkyl, alkenyl or alkynyl);

or (iii) a steroid derivative wherein R$^3$ and/or R$^{17}$ are other than hydrogen may be obtained from the corresponding compound wherein R$^3$ and/or R$^{17}$ are hydrogen by a conventional etherification or esterification process;

or (iv) a steroid derivative wherein R$^3$ and/or R$^{17}$ are hydrogen may be obtained by hydrolysis of the corresponding compound wherein R$^3$ and/or R$^{17}$ are other than hydrogen;

or (v) a steroid derivative wherein A is alkenylene may be hydrogenated to provide the corresponding compound wherein A is alkylene;

or (vi) a steroid derivative wherein —X— is —CH$_2$NR$^2$— or —NR$^2$CH$_2$— may be obtained by the reduction of the corresponding compound wherein —X— is —CONR$^2$— or —NR$^2$CO—;

or (vii) a steroid derivative wherein —X— is —CSNH— or —NHCS— may be obtained by the reaction of the corresponding compound wherein X is —CONH— or —NHCO— with 2,4-bis-(4- methoxyphenyl)-1,3-dithia-2,4-diphosphetane-2,4-disulphide;

or (viii) a steroid derivative wherein X is —(NO)R$^2$, —SO— or —SO$_2$— may be obtained by the oxidation of the corresponding compound wherein X is —NR$^2$— or —S—.

5. A pharmaceutical composition comprising a steroid derivative, claimed in claim 1, together with a pharmaceutical acceptable diluent or carrier.

6. A composition as claimed in claim 5 which is suitable for oral administration and which contains from 5 to 500 mg. of a steroid derivative.

7. A method for producing an antioestrogenic effect in a warm-blooded animal in need of such treatment, which comprises administering to said animal an effective amount of at least one steroid derivative as claimed in claim 1.

8. A compound selected from the group consisting of N-n-butyl-N-methyl-, N-2,2,3,3,4,4,4-heptafluorobutyl-N-methyl- and N,N-(3-methylpentamethylene)-11-(3,17β-dihydroxyoestra-1,3,5(10)-trien-7α-yl)undecamide;

N-n-butyl- and N-2,2,3,3,4,4,4-heptafluorobutyl-3-p-[4-(3,17β-dihydroxyoestra-1,3,5(10)-trien-7α-yl)butyl]phenylpropionamide;

7α-(10-p-chlorophenylthiodecyl)-, 7α-(10-p-chlorophenylsulphinyldecyl)-, 7α-[9-(4,4,5,5,5-pentafluoropentylsulphinyl)nonyl]-, 7α-[10-[4,4,4-trifluorobutylsulphinyl)decyl]- and 7α-[10-p-chlorobenzylsulphinyl)-decyl]oestra-1,3,5(10)-triene-3,17β-diol; and 7α-(9-n-heptylsulphinylnonyl)oestra-1,3,5(10)-triene-3,17β-diol.

* * * * *

UNITED STATES PATENT AND TRADEMARK OFFICE
CERTIFICATE OF CORRECTION

PATENT NO. : 4,659,516  
DATED : April 21, 1987  
INVENTOR(S) : Rowler et al.

It is certified that error appears in the above-identified patent and that said Letters Patent is hereby corrected as shown below:

Column 3,  
Lines 58-65, change 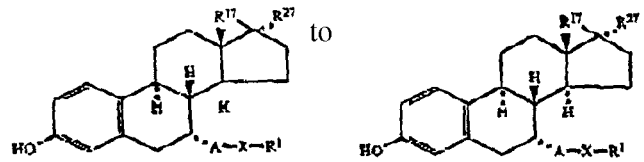 to

Column 36,  
Lines 1-10, change 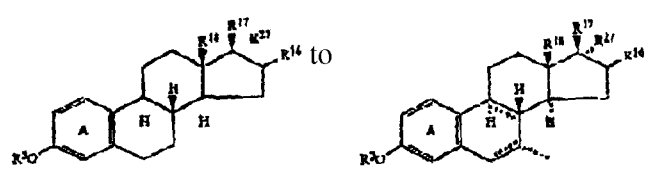 to

Column 37,  
Lines 17-25, change 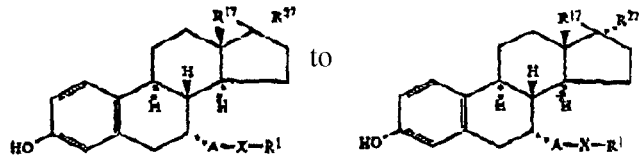 to

Signed and Sealed this

Fifteenth Day of July, 2003

JAMES E. ROGAN  
*Director of the United States Patent and Trademark Office*